United States Patent
Ferguson et al.

(10) Patent No.: US 7,553,273 B2
(45) Date of Patent: Jun. 30, 2009

(54) APPARATUS AND METHOD FOR MANAGING INCONTINENCE

(75) Inventors: Joe W. Ferguson, Collierville, TN (US); Carlos E. Gil, Collierville, TN (US)

(73) Assignee: Duodyn Technology, LLC, Collierville, TN (US)

( * ) Notice: Subject to any disclaimer, the term of this patent is extended or adjusted under 35 U.S.C. 154(b) by 30 days.

(21) Appl. No.: 11/742,675

(22) Filed: May 1, 2007

(65) Prior Publication Data

US 2007/0282161 A1    Dec. 6, 2007

Related U.S. Application Data

(60) Provisional application No. 60/864,751, filed on Nov. 7, 2006, provisional application No. 60/746,092, filed on May 1, 2006.

(51) Int. Cl.
*A61F 2/00*    (2006.01)
(52) U.S. Cl. .................................................. 600/29
(58) Field of Classification Search ............. 600/29–32; 604/332, 334; 128/897
See application file for complete search history.

(56) References Cited

U.S. PATENT DOCUMENTS

| | | | |
|---|---|---|---|
| 3,570,489 | A | 3/1971 | Brown |
| 3,938,521 | A | 2/1976 | Ritoa et al. |
| 4,686,985 | A | 8/1987 | Lottick |
| 4,950,223 | A * | 8/1990 | Silvanov ............... 600/32 |
| 4,979,947 | A | 12/1990 | Berman |
| 4,986,822 | A | 1/1991 | Anderson |

(Continued)

FOREIGN PATENT DOCUMENTS

DE    4436796    4/1996

(Continued)

OTHER PUBLICATIONS

International Search Report dated Oct. 25, 2007, mailed Feb. 28, 2008 for PCT Application Serial No. PCTUS2007/067897, 18 pages.

(Continued)

*Primary Examiner*—Charles A Marmor, II
*Assistant Examiner*—Christine D Hopkins
(74) *Attorney, Agent, or Firm*—Arent Fox LLP; James J. Bindseil

(57) ABSTRACT

An incontinence management device comprises a head having a first state and a second state. In the first state, the head is sized for insertion within a predetermined body orifice or cavity. In the second state, the head is sized to substantially seal the predetermined body orifice or cavity. In an aspect of use in an anal cavity, the device is configured so that the head forms a seal above the dentate line within the anal cavity. Further, in some aspects, the head substantially comprises a resorbable material. Additionally, in other aspects, the device further comprises a base, which limits insertion of the device within the body orifice, and an activator mechanism in communication with the head and movable relative to the base between a first position and a second position. The movement of the activator mechanism between the first position and the second position correspondingly causes the head to change between the first state and the second state or vice versa.

30 Claims, 16 Drawing Sheets

U.S. PATENT DOCUMENTS

| | | |
|---|---|---|
| 5,401,776 A | 3/1995 | Laurent |
| 5,421,827 A | 6/1995 | Temple |
| 5,509,889 A | 4/1996 | Kalb et al. |
| 5,513,659 A | 5/1996 | Buuck et al. |
| 5,569,216 A | 10/1996 | Kim |
| 5,695,484 A | 12/1997 | Cox |
| 5,782,745 A | 7/1998 | Benderev |
| 5,800,338 A | 9/1998 | Kollerup et al. |
| 6,013,023 A | 1/2000 | Klingenstein |
| 6,042,534 A | 3/2000 | Gellman et al. |
| 6,096,057 A | 8/2000 | Klingenstein |
| 6,251,064 B1 | 6/2001 | Silverman |
| 6,334,446 B1 | 1/2002 | Beyar |
| 6,485,476 B1 * | 11/2002 | von Dyck et al. ........... 604/332 |
| 6,491,623 B2 | 12/2002 | Snyder |
| 6,527,755 B1 | 3/2003 | Salama |
| 6,533,717 B2 | 3/2003 | Silverman et al. |
| 6,843,766 B1 | 1/2005 | Nemir |
| 6,862,480 B2 | 3/2005 | Cohen et al. |
| 6,905,471 B2 | 6/2005 | Leivseth et al. |
| 6,913,573 B1 | 7/2005 | Viscomi et al. |
| 6,915,165 B2 | 7/2005 | Forsell |
| 6,916,312 B2 | 7/2005 | Kondo et al. |
| 6,926,701 B2 | 8/2005 | Burns, Jr. et al. |
| 2001/0018548 A1 | 8/2001 | Sliverman et al. |
| 2001/0041823 A1 | 11/2001 | Snyder et al. |
| 2004/0037887 A1 | 2/2004 | Bourne et al. |
| 2004/0133197 A1 * | 7/2004 | Utley et al. ................... 606/41 |
| 2005/0065616 A1 | 3/2005 | Ankorina-Stark et al. |
| 2005/0113859 A1 | 5/2005 | Elliott et al. |

FOREIGN PATENT DOCUMENTS

| | | |
|---|---|---|
| DE | 102004033425 | 1/2006 |
| EP | 0218203 | 5/1991 |
| WO | 9007311 | 7/1990 |
| WO | 9426215 | 11/1994 |
| WO | 9639097 | 12/1996 |
| WO | WO 97/17908 | 5/1997 |
| WO | 9745066 | 12/1997 |
| WO | WO 98/01088 | 1/1998 |
| WO | WO 98/27971 | 7/1998 |
| WO | WO 98/33458 | 8/1998 |
| WO | WO 02/065975 | 8/2002 |
| WO | WO 2004/093724 | 11/2004 |
| WO | WO 2005/014073 | 2/2005 |
| WO | WO 2005/055958 | 6/2005 |
| WO | WO 2005/082276 | 9/2005 |

OTHER PUBLICATIONS

Notification Of Transmittal Of The International Search Report And The Written Opinion Of The International Searching Authority, Or The Declaration, mailed Feb. 28, 2008 in corresponding International Application No. PCT/US2007/067897, 20 pages.

* cited by examiner

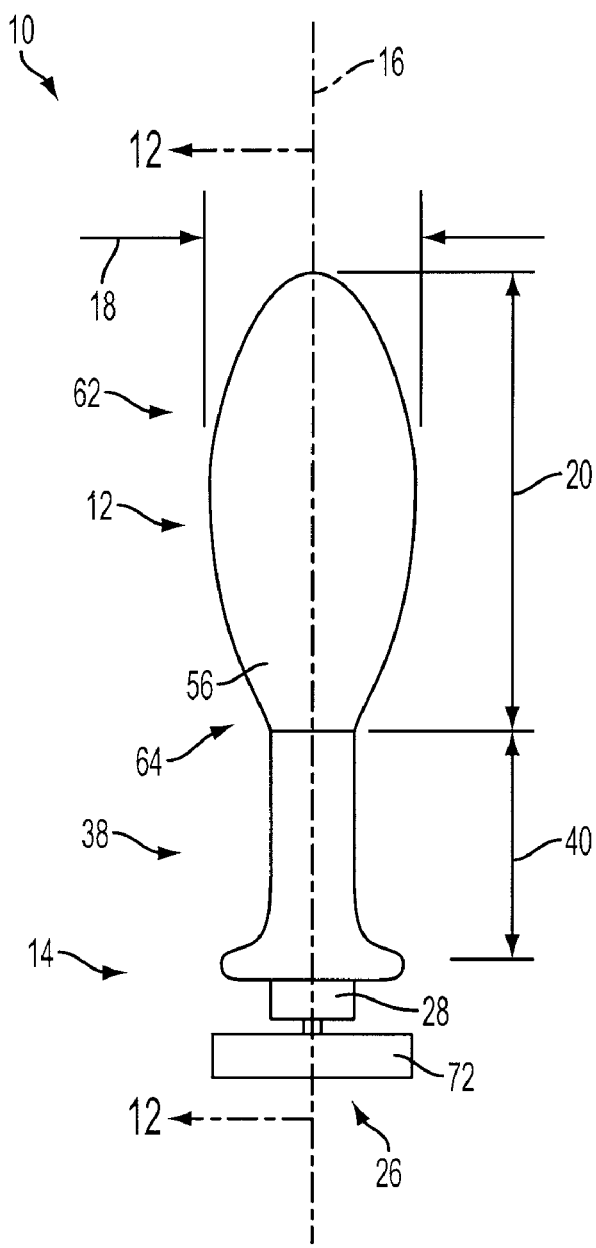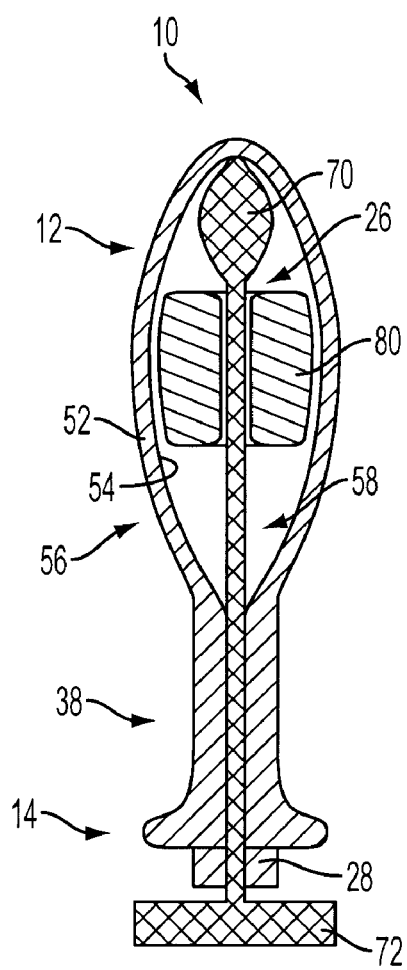
FIG. 11
FIG. 12

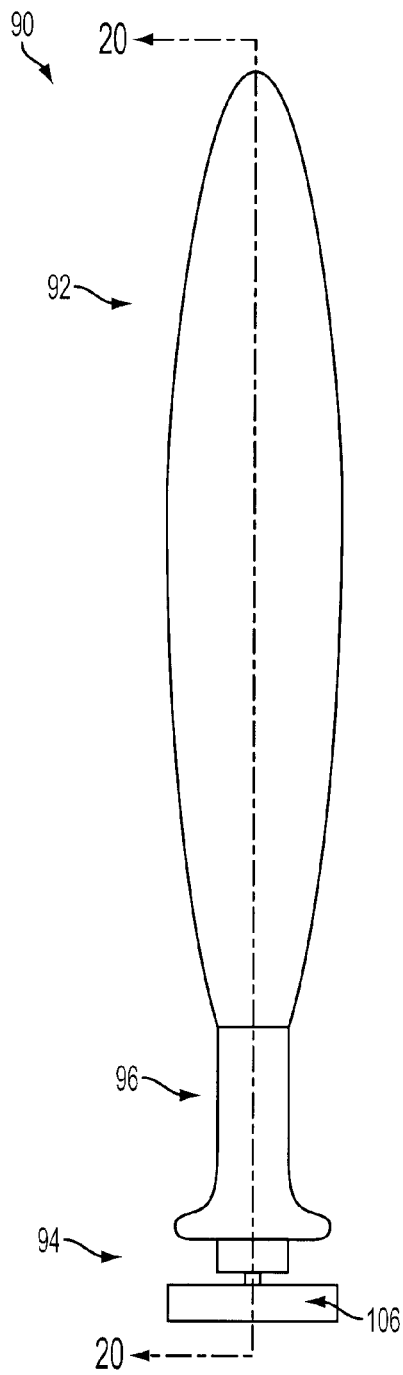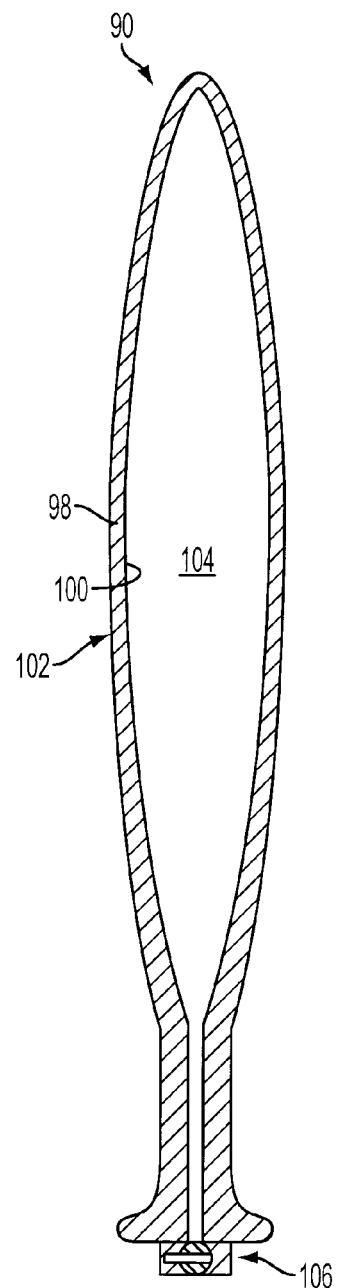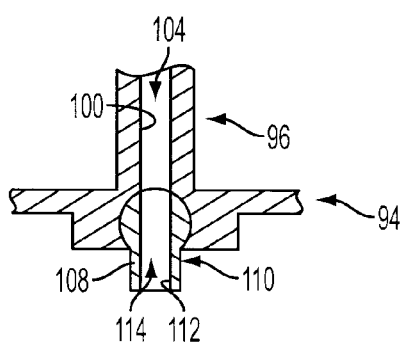
FIG. 19
FIG. 20
FIG. 21

APPARATUS AND METHOD FOR MANAGING INCONTINENCE

CLAIM OF PRIORITY UNDER 35 U.S.C. §119

The present Application for Patent claims the benefit of Provisional Application No. 60/864,751 entitled "APPARATUS AND METHOD FOR MANAGING INCONTINENCE" filed Nov. 7, 2006, and Provisional Application No. 60/746,092 entitled "APPARATUS AND METHOD FOR MANAGING INCONTINENCE" filed May 1, 2006, each hereby expressly incorporated by reference herein.

BACKGROUND

The described aspects relate to controlling the discharge of waste products from a bodily orifice, referred to as incontinence, and more particularly, to apparatus and methods for managing incontinence.

Many people have trouble controlling their urinary and fecal bodily functions, for example, due to age, stress, surgical procedures, drug therapies, child birth, etc. It has been reported that over 5.5 million people age 55 and older report this problem per year. Additionally, it is believed that many more people do not report this problem in order to avoid embarrassment, or because of the belief that it is an unavoidable problem related to getting old.

A number of prior art devices have attempted to address the need of assisting in controlling urinary and fecal bodily functions, however, each of these alleged solutions have drawbacks. For example, some devices rely solely on absorbent material to stop the unwanted flow of bodily waste products. Such devices, however, may not provide sufficient blockage of bodily waste products. Additionally, other devices provide an air-tight seal that does not allow the flow of gases that may build up, which may result in heightened levels of discomfort for the user. Additionally, other known devices are known to irritate sensitive tissue, causing discomfort for the user.

Thus, improved devices and methods for managing incontinence are desired.

SUMMARY

The described aspects provide devices and methods for managing incontinence, and/or for controlling the flow of digestive by-products from a bodily cavity.

In an aspect, an incontinence management device comprises a base sized to limit insertion of the incontinence management device into an anal cavity having a dentate line. The device further includes a head having a first state and a second state, wherein in the first state the head is sized for insertion within the anal cavity, and wherein in the second state the head is sized to substantially seal the anal cavity above the dentate line. Additionally, the device includes a neck connected to and extending between the base and the head. The neck comprises a predetermined length to position the head beyond the dentate line when the incontinence management device is located at deployed position within the anal cavity.

In another aspect, an incontinence management device comprises means for limiting insertion of the device into an anal cavity. The device further includes means for sealing having a first state and a second state, wherein in the first state the means for sealing is sized for insertion within the anal cavity, and wherein in the second state the means for sealing is sized to substantially seal the anal cavity above the dentate line. Additionally, the device includes means for connecting the means for limiting insertion and the means for sealing, the means for connecting extending between the means for limiting insertion and the means for sealing, wherein the means for connecting comprises a predetermined length to position the means for sealing beyond the dentate line when the incontinence management device is located at a deployed position within the anal cavity.

In an aspect, a method of managing incontinence comprises obtaining a device comprising: a base sized to limit insertion of the incontinence management device into the anal cavity; a head connected to the neck, the head having a first state and a second state, wherein in the first state the head is sized for insertion within the anal cavity, and wherein in the second state the head is sized to substantially seal the anal cavity; and a neck connected to and extending between the base and the head, wherein the neck comprises a predetermined length to position the head beyond the dentate line when the incontinence management device is located at an operating position within the anal cavity. The method further includes inserting the device, with the head in the first state, through an external opening and into an anal cavity such that the head precedes the neck and the base. Additionally, the method includes positioning the device within the anal cavity so that the head is inserted beyond the dentate line within the anal cavity, and so that the head is operable to change to the second state and form a seal with the anal cavity at a location within the anal cavity beyond the dentate line.

In some aspects, an incontinence management device comprises a head having a first state and a second state. In the first state, the head is sized for insertion within a predetermined body orifice operable to eject digestive by-products. In the second state, the head is sized to substantially seal the predetermined body orifice. Further, the head substantially comprises a resorbable material.

In other aspects, an incontinence management device comprises a base and a head extending from the base and having an internal wall defining an internal chamber. The head comprises a length parallel to a first axis and a width parallel to a second axis. Further, the head is movable between a first shape having a first width operable to permit insertion into a bodily cavity and a second shape having a second width operable to seal the anal cavity. Additionally, the device comprises an activator mechanism in communication with the head and movable relative to the base between a first position and a second position. The movement of the activator mechanism between the first position and the second position correspondingly causes the head to change between the first shape and the second shape.

In still other aspects, an incontinence management device comprises a base and a head extending from the base. The head has a length parallel to a first axis and a width parallel to a second axis. Further, the head is movable between a first shape having a first width operable to permit insertion into a body opening operable to eject digestive by-products and a second shape having a second width operable to seal the body opening. Additionally, the device includes an activator mechanism in communication with the head and movable relative to the base between a first position and a second position. Movement of the activator mechanism between the first position and the second position correspondingly causes the head to change between the first shape and the second shape.

BRIEF DESCRIPTION OF THE DRAWINGS

FIG. 11 is a side view of the device of FIG. 9 in an insertion state;

FIG. 12 is a cross-sectional view of the device of FIG. 3 along line 12-12;

FIG. 19 is a side view of another aspect of an incontinence management device in an insertion state, similar to FIG. 11;

FIG. 20 is a cross-sectional view of the incontinence management device of FIG. 19 along line 20-20, with an aspect of an activator mechanism in a first or closed state;

FIG. 21 is an enlarged, partial cross-sectional view of the activator mechanism of FIG. 20 in a second or open state;

DETAILED DESCRIPTION

Figure 1:
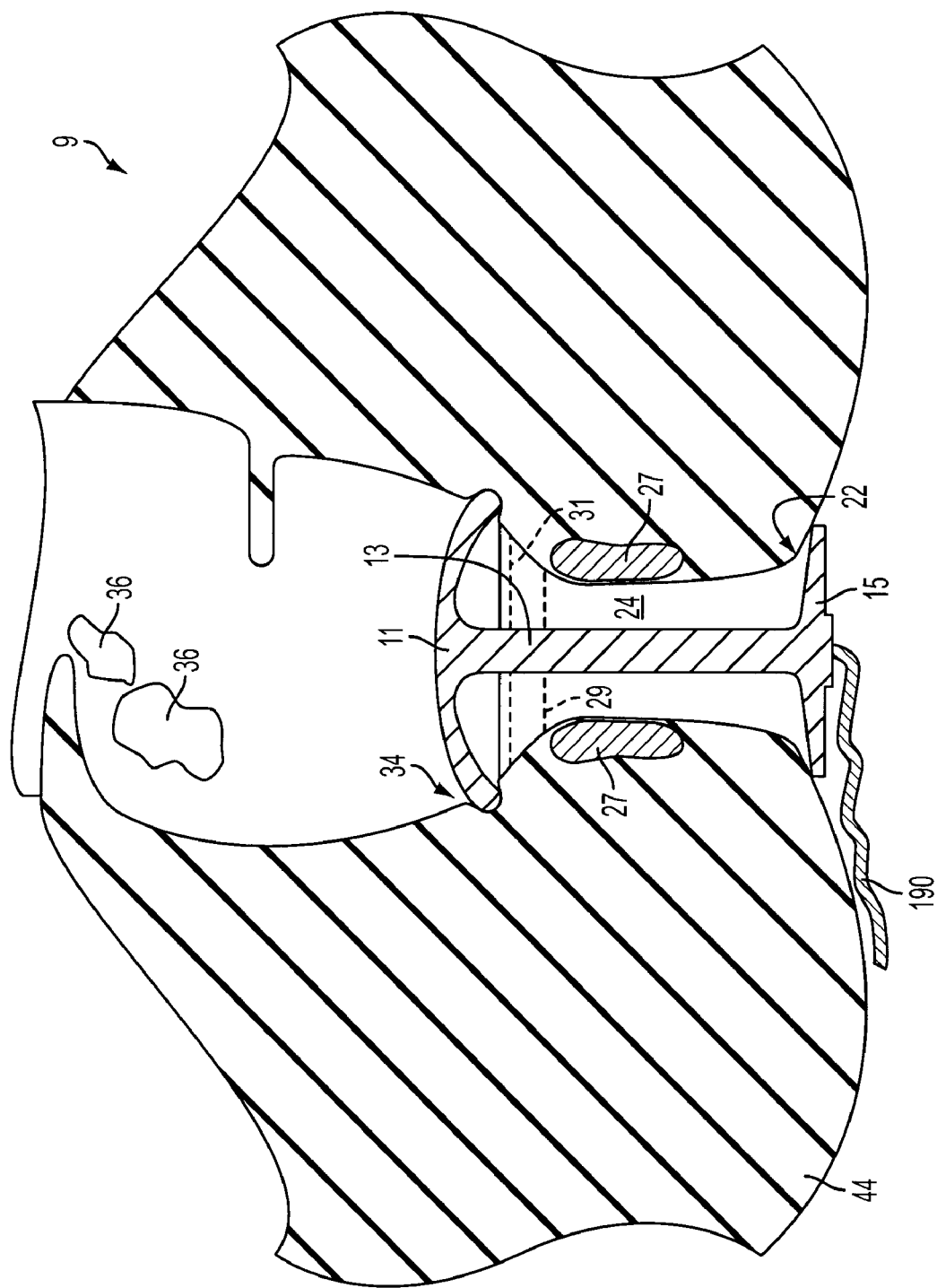
FIG. 1 is a partial cross-sectional view of an aspect of an incontinence management device in a deployed state within a bodily cavity.
Figure 2:
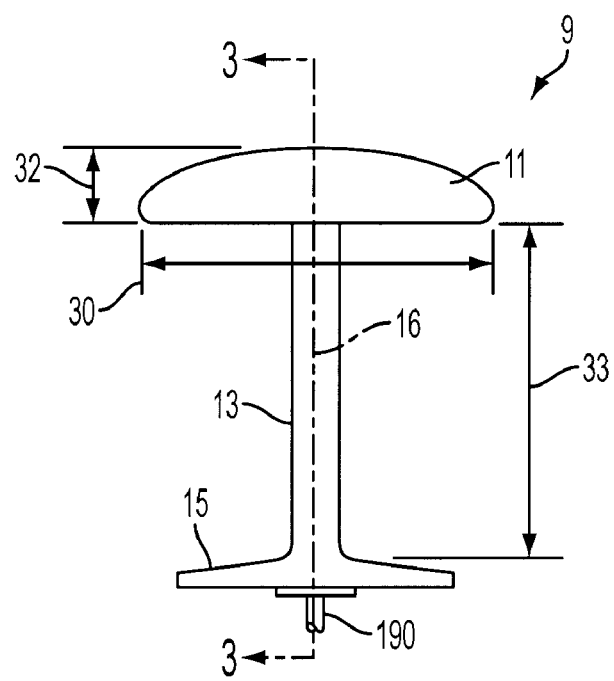
FIG. 2 is a side view of the device of FIG. 1.
Figure 3:
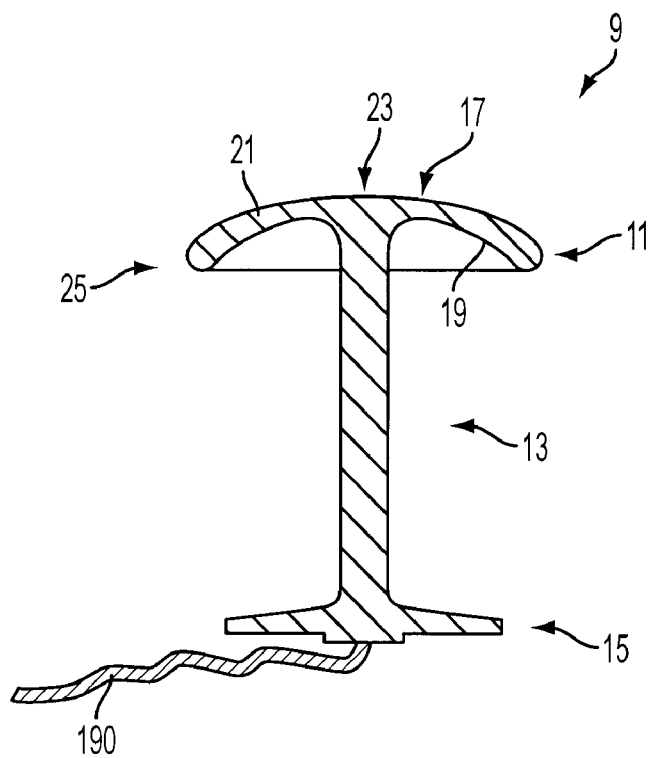
FIG. 3 is a cross-sectional view of the device of FIG. 2 along line 3-3.
Figure 4:
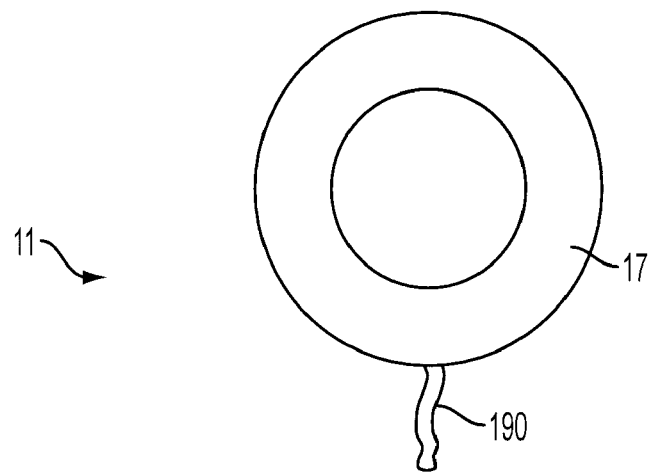
FIG. 4 is a top view of the device of FIG. 2.
Figure 5:
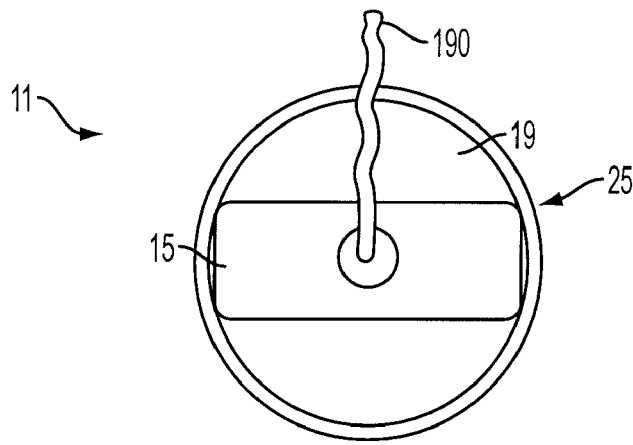
FIG. 5 is a bottom view of the device of FIG. 2.
Figure 6:
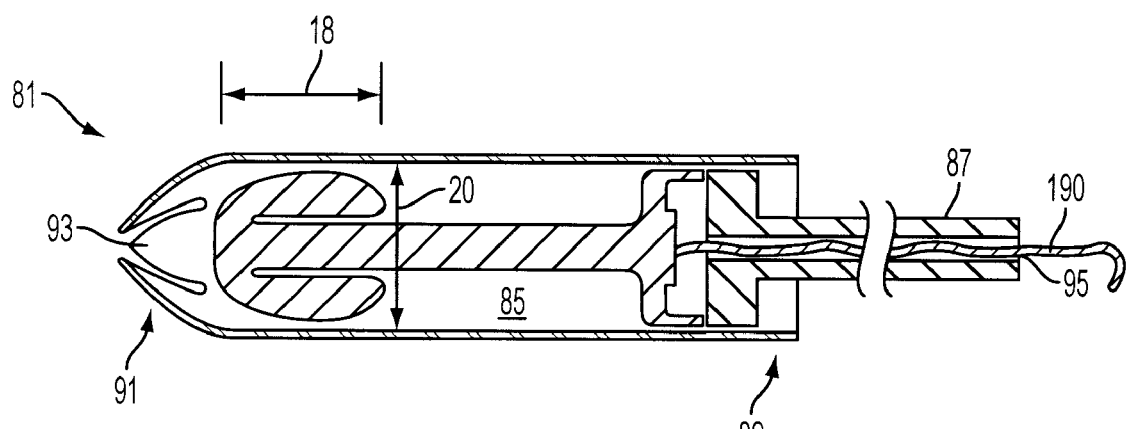
FIG. 6 is a cross-sectional view of an aspect of a deployment mechanism operable to deploy the device of FIG. 1 into the bodily cavity of FIG. 1.

The present apparatus and methods now will be described more fully with reference to the accompanying drawings, in which aspects of the invention are shown. The apparatus and methods may be embodied in many different forms, however, and should not be construed as limited to the aspects set forth herein; rather, these aspects are provided so that this disclosure will be thorough and complete, and will fully convey the scope of the invention to those skilled in the art. Additionally, throughout this description, like numbers refer to like elements.

Referring to FIGS. 1-7, in an aspect, apparatus and methods of controlling incontinence comprise an incontinence management device 9 having a head 11 connected to a neck 13 extending along a longitudinal axis 16 (FIG. 1) from a base 15. Head 11 is movable between an insertion state (FIG. 6) and a deployed state (FIGS. 1-5 and 7). In the insertion state (FIG. 6), head 11 has a first shape, comprising an insertion width 18 and an insertion height 20, sized for inserting device 9 through a body opening 22 and at least partially into bodily cavity 24. For example, in some aspects, bodily cavity 24 may comprise any orifice within an animal body 44 from which bodily gaseous and/or liquid fluids may escape, while in other aspects, bodily cavity 24 may comprise an orifice, such as an anus and/or a urethra, operable to expel bodily waste products. Insertion width 18 comprises a measure of a dimension of head 12 extending away from longitudinal axis 16, while insertion height 20 comprises a measure of a dimension of head 12 extending along longitudinal axis 16.

Additionally, in the deployed state (FIGS. 1-5 and 7), head 11 has a second shape, comprising a deployment width 30 and a deployment height 32, sized to create a seal 34 (FIGS. 1 and 7) between device 9 and bodily cavity 24 to substantially prevent bodily fluids, waste and/or excrement 36 (FIGS. 1 and 7) within cavity 24 from being discharged through opening 22. Deployment width 30 is a measure of head 11 extending substantially parallel to insertion width 18, where deployment width 30 is greater than, and in some aspects substantially greater than, insertion width 18. Similarly, deployment height 32 is a measure of head 12 extending substantially parallel to and, at least in some aspects, greater than or substantially greater than, insertion height 20.

Additionally, in the deployed state (FIGS. 1-5 and 7), head 11 is defined by an external surface 17 and an opposing internal surface 19. Head 11 may have any shape configured to form seal 34. In one preferred aspect, for example, external surface 17 includes, at least in part, a convex shape, while internal surface 19 includes, at least in part, a concave surface. As such, in this aspect, head 11 includes, at least in part, a curved section 21 between an apex 23 and an end 25 when viewed in a cross-section taken through head 11 along a plane intersecting axis 16. Further, in this aspect, curved section 21 provides head 11 with an elastic characteristic that allows head 11 to be securely retained within bodily cavity 24 and additionally resists forces applied by bodily fluids, waste and/or excrement 36 that would tend to urge incontinence management device 9 out of the deployed position (FIGS. 1 and 7) within bodily cavity 24.

Additionally, in an aspect where bodily cavity 24 comprises an anal cavity, head 11 is positioned far enough inside cavity 24 in the deployed state to form seal 34 at a location beyond sensitive nerve endings 27 within anal canal. Generally, for example, sensitive nerve endings 27 may be positioned within the anal canal between opening 22 and a dentate line 29, also referred to as a pectinate line. As such, in one preferred aspect, head 11 may be positioned within the anal canal above dentate line 29 so as to avoid irritating sensitive nerve endings 27. For example, dentate line 29 may be located about 2.5 (centimeters) cm to about 3 cm within the anal canal beyond opening 22. As such, in one aspect, head 11 may be positioned to form seal 34 at a location greater than about 2.5 cm past opening 22. In another aspect, to insure that head 11 avoids contacting sensitive nerve endings 27 in a typical anal canal, head 11 may be positioned to form seal 34 at a location greater than about 3 cm past opening 22. In another aspect, head 11 may be positioned to form seal 34 at a location greater than about 4 cm past opening 22. In a further aspect, head 11 may be positioned to form seal 34 between dentate line 29 and an anorectal line 31, which is typically about 4 cm to about 5 cm from opening 22. Further, in this aspect, head 11 may have deployment width 30 in a diameter ranging from about 1.5 cm to about 5 cm, and more preferably from about 2.5 cm to about 4.5 cm, thereby allowing head 11 to occlude the anal cavity at a location beyond dentate line 29. Thus, head 11 may be positioned to form seal 34 at a location within anal canal greater than about 2.5 cm, or at a location greater than about 2.5 cm to about 5 cm from opening 22.

Correspondingly, in some aspects, incontinence management device 9 may be configured such that neck 13 has a predetermined length 33, so that upon insertion of device 9, when base 15 contacts opening 22 or an external area adjacent to opening 22, head 11 is spaced from base 15 so as to form seal 34 between above dentate line 29, or between dentate line 29 and anorectal line 31. For example, in various aspects, predetermined length 33 may be greater than about 2.5 cm, or greater than about 3 cm, or greater than about 4 cm, or in the range from greater than about 2.5 cm to about 5 cm.

Further, as discussed in more detail below, device 9 may be formed from any biocompatible material. Further, in some aspects, device 9 may be formed, at least in part, by a biodegradable material. For example, device 9 may be formed from a biodegradable material having a predetermined degradation rate inside the anal cavity, thereby allowing the device to degrade within the anal cavity according to a predetermined biodegradation characteristic Additionally, as discussed in more detail below, device 9 may comprise a therapeutic agent, which may be releasably contained within the material of device 9, or which may be applied to the material of device 9, or which may be contained within a carrier or carrier layer applied to device 9.

Further, as discussed in more detail below, device 9 may further include head 11 having a permeable section 74 (see, e.g., FIG. 10), such as to allow the passage of liquid or gas.

Figure 10:
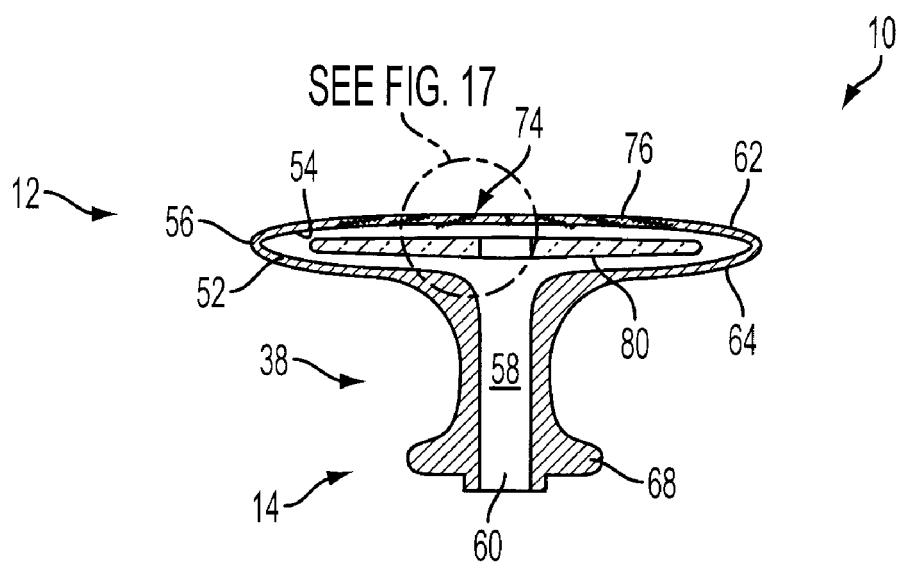
FIG. 10 is a cross-sectional view of the device of FIG. 9 along line 10-10.

Additionally, in some aspects, device 9 may include an internal cavity 58 (see, e.g., FIG. 10). In further aspects, a scaffold structure 80 (see, e.g., FIG. 10) may be located within internal chamber 58, in particular within the head.

Figure 27:
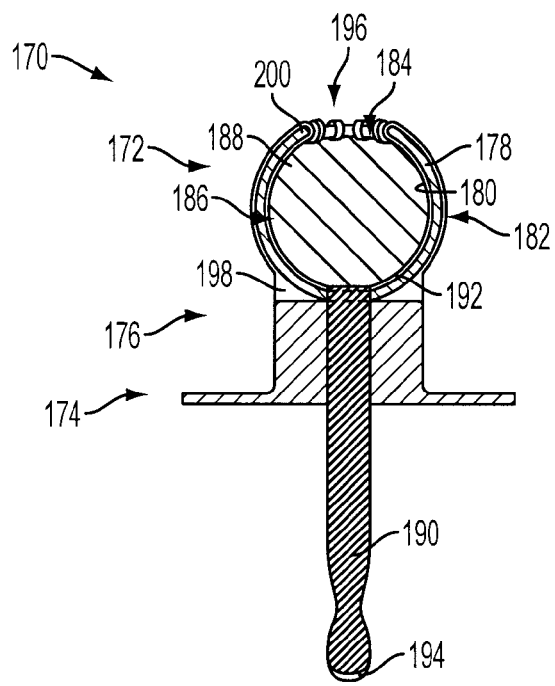
FIG. 27 is a cross-sectional view of the device of FIG. 26 along line 27-27.
Figure 28:
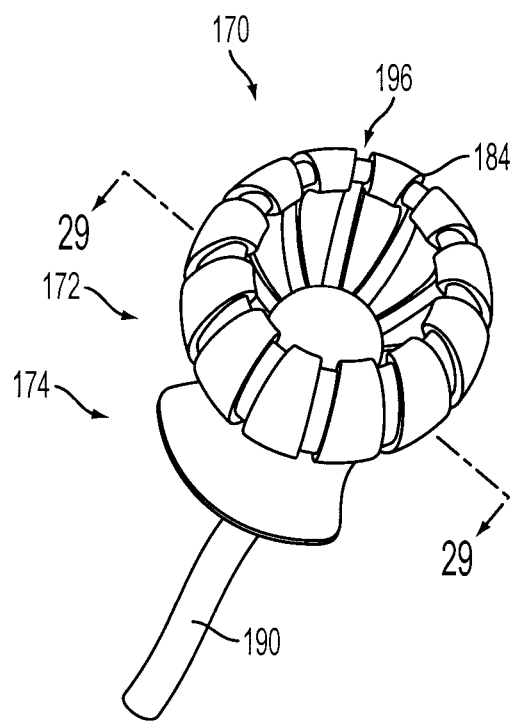
FIG. 28 is a perspective view of the device of FIG. 26 in a deployment state.
Figure 29:
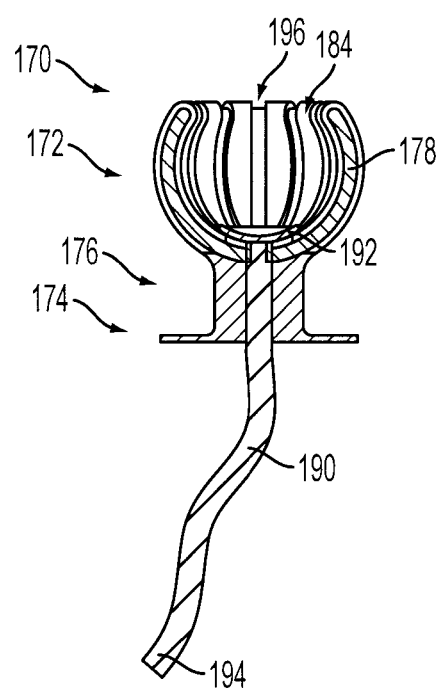
FIG. 29 is a cross-sectional view of the device of FIG. 28 along line 29-29.

Optionally, device 9 may include retrieval mechanism 190 (see, e.g., FIG. 27) to allow a user to remove device 9 from deployed position (FIGS. 1 and 7) within bodily cavity 24.

Figure 7:
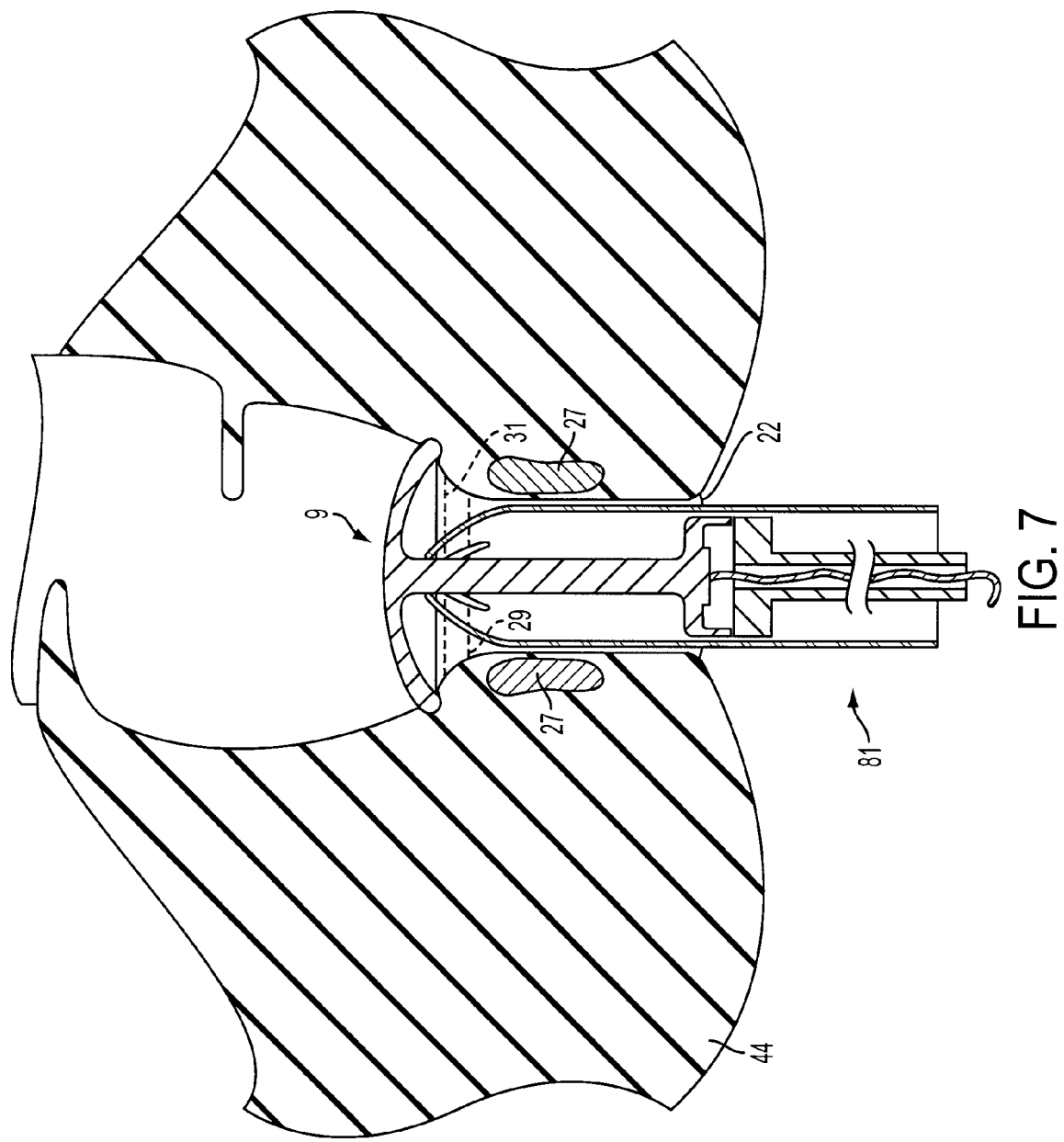
FIG. 7 is a partial cross-sectional view of an aspect of an operation of the deployment mechanism of FIG. 6 deploying the device of FIG. 2.

Optionally, device 9 may further include a deployment mechanism 81 (FIGS. 6-7; also see, e.g., 181 in FIG. 18) to assist with inserting device 9 in bodily cavity 24 and to assist in changing head 11 from the insertion state (FIG. 6) to the deployed state (FIG. 7). For example, device 9 may be contained within deployment mechanism 81 (FIG. 6), such as a hollow cylindrical body having a wall that defines an internal cavity 85 that restricts the size of head 11. Deployment mechanism 81 may also include an activator mechanism 87, such as a plunger, positioned at an open end 89 of deployment mechanism and operable by a user to urge device 9 out of internal cavity 85 through insertion end 91. Insertion end 91 may include one or more flaps 93 that are movable between at least a first position (FIG. 6) to cover insertion end 91 and a second position to allow device 9 to move into bodily cavity 24 (see, e.g., FIG. 7). Optionally, activator mechanism 87 may include a passageway 95, such as an internal wall defining an internal cavity, operable to allow retrieval mechanism 190 to extend out of deployment mechanism 81. Deployment mechanism 81 thereby maintains at least insertion width 18, and optionally insertion height 20, until device 9 is deployed within bodily cavity 24.

Figure 8:
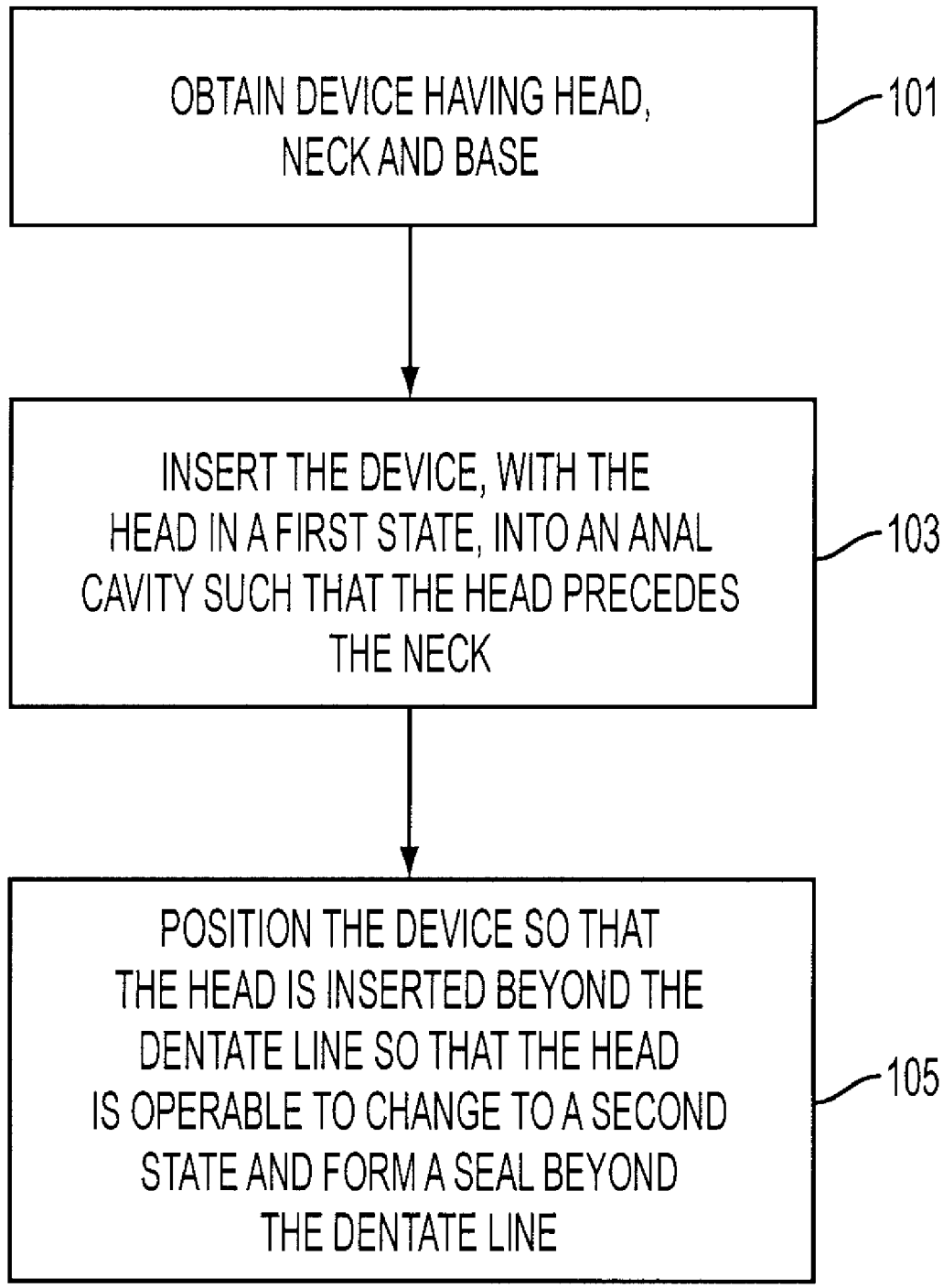
FIG. 8 is a flowchart of an aspect of a method for managing incontinence.

Referring to FIG. 8, one aspect of a method of managing incontinence comprises obtaining a device having the above-described head 11, neck 13 and base 15 (Block 101). The method further includes inserting the device, with the head in the first state, through an external opening and into an anal cavity such that the head precedes the neck and the base (Block 103). And, the method includes positioning the device within the anal cavity so that the head is inserted beyond the dentate line within the anal cavity, and so that the head is operable to change to the second state and form a seal with the anal cavity at a location within the anal cavity beyond the dentate line (Block 105).

Optionally, the method may further include one or more of: containing the device within a deployment mechanism having an activator mechanism, inserting the deployment mechanism within the anal cavity, and moving the activator mechanism to deploy the device; allowing the device to degrade within the anal cavity according to a predetermined biodegradation characteristic; releasing a therapeutic agent from the device; allowing gas to pass through the device; and removing the device from the anal cavity using a retrieval mechanism.

Figure 13:
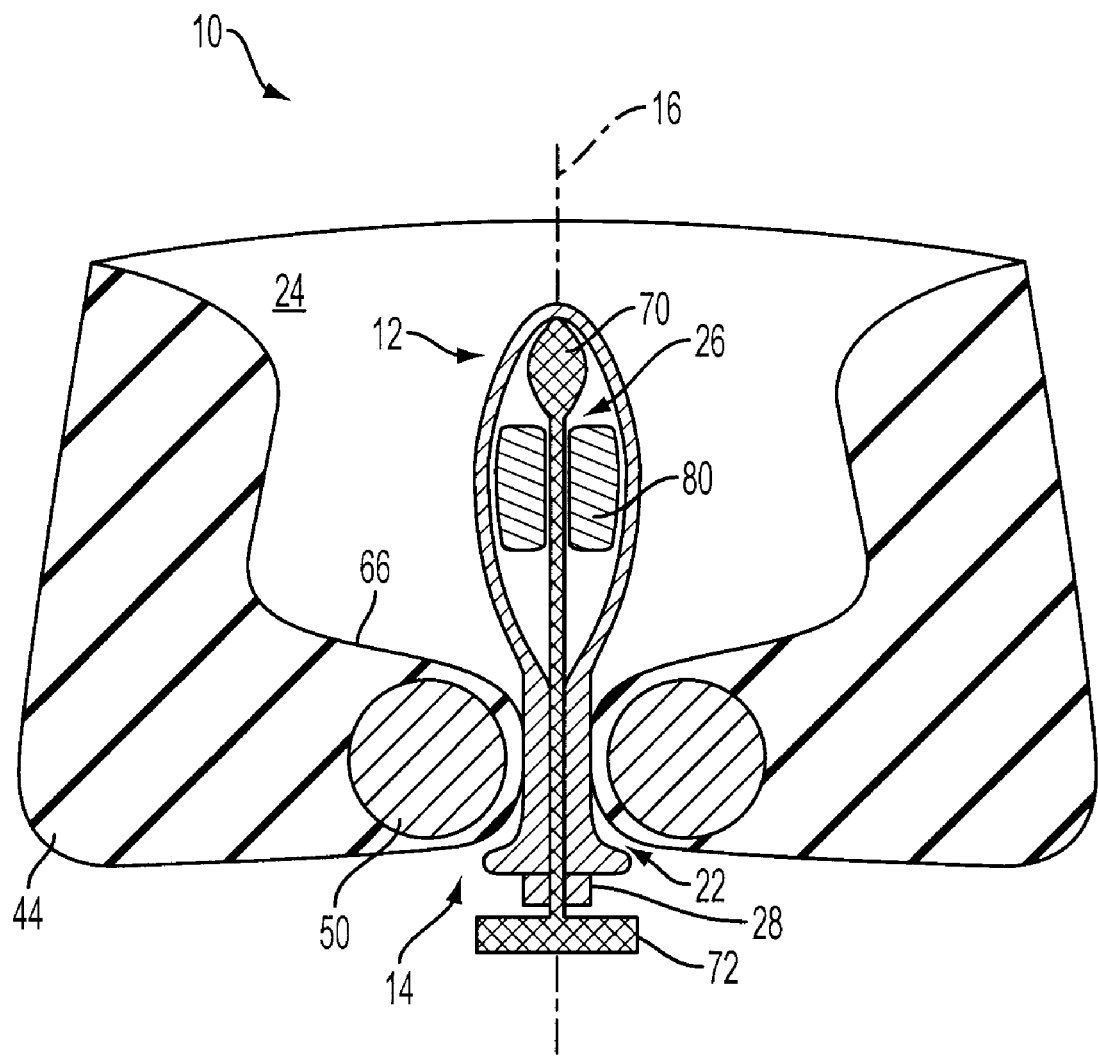
FIG. 13 is a partial cross-sectional view of the device of FIG. 9, in the insertion state, inserted through one aspect of a bodily opening and positioned within the opening and within a bodily cavity connected to the opening.

Referring to FIGS. 9-18, in some aspects, apparatus and methods for controlling incontinence comprise an incontinence management device 10 having a head 12 extending from a base 14 along a longitudinal axis 16 (FIG. 9), where head 12 is movable between a deployed state (FIGS. 9, 10 and 14-18) and an insertion state (FIGS. 11-13 and 18). In some aspects, for example, head 12 is biased to move from the insertion state into the deployed state, while in other aspects, the biasing may be from the deployed state to the insertion state. In the insertion state (FIGS. 11-13 and 18), head 12 has a first shape, comprising an insertion width 18 and an insertion height 20, sized for inserting device 10 through a body opening 22 (FIG. 13) and at least partially into bodily cavity 24 (FIG. 13). For example, in some aspects, bodily cavity 24 may comprise any orifice within an animal body from which bodily gaseous and/or liquid fluids may escape, while in other aspects, bodily cavity 24 may comprise an orifice, such as an anus and/or a urethra, operable to expel bodily waste products. Insertion width 18 comprises a measure of a dimension of head 12 extending away from longitudinal axis 16, while insertion height 20 comprises a measure of a dimension of head 12 extending along longitudinal axis 16. Further, in the insertion state, device 10 includes an activator mechanism 26 (FIGS. 11-13), such as a relatively rigid stem, which contacts head 12 and maintains at least insertion width 18, and optionally insertion height 20, until device 10 is ready for deployment. Optionally, base 14 may include a locking mechanism 28 to removably secure activator mechanism 26 to device 10 to maintain the device in the insertion state.

To deploy device 10, activator mechanism 26 is removed from contact with head 12, and may be entirely disconnected from the device, and device 10 moves into the deployed state due to the above-mentioned bias. In the deployed state (FIGS. 9, 10 and 14-18), head 12 has a second shape, comprising a deployment width 30 and a deployment height 32, sized to create a seal 34 (FIG. 14) between device 10 and bodily cavity 24 and/or opening 22 to substantially prevent bodily fluids, waste and/or excrement 36 (FIG. 14) within cavity 24 from being discharged. Deployment width 30 is a measure of head 12 extending substantially parallel to insertion width 18, where deployment width 30 is greater than, and in some aspects substantially greater than, insertion width 18. Similarly, deployment height 32 is a measure of head 12 extending substantially parallel to and, at least in some aspects greater than or substantially greater than, insertion height 20.

Figure 9:
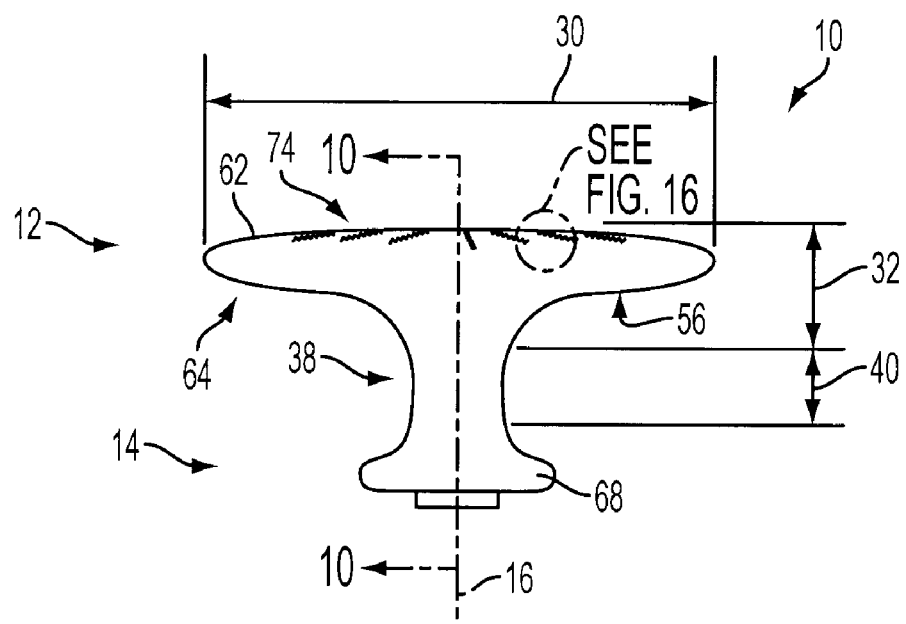
FIG. 9 is a side view of one aspect of an incontinence management device in a deployed state.

Further, a neck 38 may extend substantially parallel to axis 16 to connect and position head 12 and base 14 at a predetermined distance 40 (FIGS. 9 and 12). Predetermined distance 40 may be sized based on or to substantially correspond to a length of opening 22, which may facilitate the sealing of opening 20 and/or cavity 22 by device 10. Additionally, base 14 is sized to extend away from longitudinal axis 16 to limit the amount that device 10 may be inserted into opening 22. Further, upon deployment, an annular portion 42 (FIG. 14) of body 44 adjacent to opening 22 is contained between portions 46 (FIG. 14) of head 12 and portions 48 (FIG. 14) of base 14. For example, in aspects where device 10 is utilized to control fecal incontinence, annular portion 42 may comprise the tissue that defines opening 22, which may include or be adjacent to a sphincter muscle 50 (FIGS. 13-14) normally operable to open and close opening 22. Further, for example, in some aspects both portions 46 and 48 may radially extend away from longitudinal axis 16. Thus, beside sealing opening 22, the deployment and sizing of head 12, and its relative position to base 14, further define a securing mechanism operable to resist internal pressure on device 10 from within cavity 24, thereby removably securing device 10 in place to seal opening 22.

In order to remove device 10, activator mechanism 26 may be placed back into contact with head 12 to move device 10 into the insertion state, which thereby forces head 12 from the sealingly-sized second shape back toward the inserting/removal-sized first shape. As such, seal 34 between device 10 and opening 22 and/or bodily cavity 24 may be at least partially broken, thereby allowing device 10 to be removed through opening 22. As noted above, for example in some aspects, activator mechanism 26 may be secured to device 10 via locking mechanism 28 prior to removal, which may facilitate controlling the removal of device 10 through activator mechanism 26.

In some aspects, device 10 comprises an elastically deformable material that allows head 12 to move between the deployed state and the insertion state. As noted above, the deployed state comprises a natural or non-deformed shape, which is the shape to which the device is biased to return to if elastically deformed, while the insertion state comprises a deformed shape of the device. For example, device 10 may comprise a substantially elastic material, such as silicone polymers, gelatin, hydrogel, polyurethane, bio gels, polyvinyl chlorides, polypropylenes, polystyrenes, acetal copolymers, polyphenyl sulfones, polycarbonates, acrylics, polyetherketone (PEEK), polyethylenes, polyethylenes, polyethers, polyethylene terphalate (PET), polymethylmethacrylate (PMMA), and mixtures and combinations of such. It should be noted that device 10 may not be entirely elastic. For example, base 14 and neck 38 may be substantially less elastic than head 12. Further, for example, head 12 may be partially non-elastic, such that head 12 may exhibit some partial deformation after being moved into the insertion state.

Additionally, in some aspects, device 10 may comprise a bioresorbable material, which may be any material that dissolves and/or degrades in bodily liquid fluid and that is biologically compatible within an animal body. In some aspects, device 10 may entirely be formed from one or more bioresorbable materials, which may be designed to maintain the integrity of the device for a predetermined amount of time, thereby maintaining the retention of the device within opening 22. For example, device 10 may comprise bioresorbable materials designed to dissolve in a short term predetermined amount of time such as ranging from about 1 hour to about 5 hours, and/or from about 2 hours to about 4 hours. Alternatively, in other aspects, device 10 may comprise bioresorbable materials designed to dissolve in a relatively longer term predetermined amount of time such as ranging from about 6 hours to about 48 hours, and/or from about 6 hours to about 18 hours, and/or from about 12 hours to about 24 hours, and/or from about 24 hours to about 36 hours, and/or from about 30 hours to about 48 hours. The exact predetermined amount of time may depend on the particular circumstances of each use of device 10, such as the state of incontinence of the user, the frequency of meals, the frequency of assistance from a caregiver, etc. Such a bioresorbable composition of device 10 may be advantageous, for example, for users who are not able or who would have difficulty in removing device 10 on their own.

In some aspects, device 10 comprises a hollow body. For example, head 12 and neck 38 may comprise a wall 52 having an inner surface 54 and an outer surface 56. Inner surface 54 defines an internal cavity 58, and outer surface 56 defines the outer shape of head 12. Internal cavity 58 may further extend through base 14, thereby defining an opening 60 that allows access to the inside of device 10. For example, in some aspects, activator mechanism 26 may be inserted through opening 60 and into cavity 58 to contact inner surface 54 at a distal side 62 of head 12 to temporarily deform the head from the deployed state into the insertion state.

In the deployed state, distal side 62 of head 12 faces bodily cavity 24 and any fluid, waste and/or excrement 36 contained within bodily cavity 24. Additionally, head 12 further comprises a proximal side 64 that faces an internal bodily wall 66 that defines cavity 24 and/or opening 22. In some aspects, for example, substantially continuous annular contact between proximal side 64 of head 12 and internal bodily wall 66, and/or exterior surface of neck 38 and internal bodily wall 66, define seal 34 that prevents and/or reduces leakage of liquid (and in some aspects, gaseous) fluid, waste and/or excrement 36 from bodily cavity 24.

In the deployed state, head 12 may elastically deform to take the shape of at least a portion of internal bodily wall 66 defining bodily cavity 24 adjacent to opening 22, and/or of opening 22, where opening 22 may extend from bodily cavity 24 to the exterior of the given body 44. For example, in some aspects such as in a fecal incontinence device, head 12 may have a shape such as a disc-shape and/or mushroom-head shape that extends in substantially equal radial distances, relative to axis 16, within at least a part of cavity 24 in an amount to cover opening 22. In other aspects, however, head 12 may have any other shape, in the deployed state, sized to plug or seal a given bodily cavity from its corresponding bodily opening.

In some aspects, neck 38 may comprise an annular cross-section, due to internal cavity 58, extending along longitudinal axis 16 and connecting head 12 and base 14. The thickness and/or elasticity of the annular cross-section defining neck 38 may vary depending on the desired flexibility between head 12 and base 14. In some aspects, for example, neck 38 comprises a cross-sectional thickness and/or elasticity sufficient to support head 12 at a position spaced apart from base 14, such as by the amount of predetermined distance 40. Additionally, the size of internal cavity 58 extending through neck 38 may vary depending on the size of activator mechanism 26 and/or the elasticity of neck 38. For example, internal cavity 58 within neck 38 may have a smaller cross section than the size of the corresponding cross section of activator mechanism 26 if neck 38 has sufficient elasticity or deformation properties to allow activator mechanism 26 to pass through. Conversely, if neck 38 is sufficiently inelastic or sufficiently rigid so as to limit expansion, internal cavity 58 within neck 38 may have a greater cross section than the size of the corresponding cross section of activator mechanism 26. Further, depending upon the desired location of seal 34 between device 10 and internal bodily wall 66 defining opening 22 and/or cavity 24, neck 38 may be sized to contact internal bodily wall 66 within opening 22 or may be sized to avoid such contact. Additionally, it should be noted that neck 38 may have any predetermined outer shape that corresponds to the shape of a given opening 22.

In some aspects, base 14 may comprise one or more flanges 68 extending away from longitudinal axis 16. The one or more flanges 68 may be sized to engage an exterior portion of body 44 adjacent to opening 22, thereby resisting the insertion of base 14 into opening 22. For example, in aspects where device 10 is utilized to control fecal incontinence, flange 68 may be extend continuously and circumferentially about opening 22 to bodily cavity 24, while in other aspects flange may comprise a plurality of individually extending flanges positioned to limit insertion of device 10 into opening 22. Further, the thickness and/or elasticity of the one or more flanges 68 may vary depending on the amount of resistance to insertion is desired or required from base 14. Additionally, as noted above, opening 60 may be formed on a side of base 14 that is not in contact with body 44 during deployment of device 10 in order to allow for the receiving and the removal of activator mechanism 26. The size of internal cavity 58 extending through base 14 may vary depending on the size of activator mechanism 26 and/or the elasticity of base 14. For example, internal cavity 58 within base 14 may have a smaller cross section than the size of the corresponding cross section of activator mechanism 26 if base 14 has sufficient elasticity or deformation properties to allow activator mechanism 26 to pass through. Conversely, if base 14 is sufficiently inelastic or sufficiently rigid so as to limit expansion, internal cavity 58 within base 14 may have a greater cross section than the size of the corresponding cross section of activator mechanism 26.

In some aspects, as noted above, device 10 may include activator mechanism 26 to enable head 12 to move between the insertion state and the deployment state, and correspondingly between the insertion shape and the deployment shape. In some aspects, therefore, activator mechanism 26 comprises a longitudinal body extending between opposing ends. Internal cavity 58 within base 14 and/or neck 38 may guide activator mechanism 36 from opening 60 into contact with inner surface 54 of wall 52 at distal side 62 of head 12. In some aspects, activator mechanism 36 may include a blunt end 70 to contact and/or engage inner surface 54 of head 12 so as to avoid piercing wall 52 that defines distal side 62. For example, blunt end 70 may comprise one or more surfaces having a flat contour, a curved contour, a spherical contour, and combinations thereof. Further, a cross section through blunt end 70, perpendicular to axis 16, may have a greater size than a corresponding cross section through an adjacent, stem-like portion of the body of activator mechanism 36. Additionally, activator mechanism 36 may include a stop or handling end 72 opposing blunt end 70. Stop or handling end 72 may extend from base 14, outside of internal cavity 58, and my limit the relative position of activator mechanism 36 with respect to device 10 in the insertion state. Further, stop or handling end 72 may be configured to allow hand manipulation of activator mechanism 36 and/or device 10. For example, in some aspects, stop or handling end 72 may comprise one or more flanges extending at a substantially oblique and/or substantially perpendicular angle from the stem-like body of activator mechanism 36. Thus, activator mechanism 26 is movable between a first position and a second position relative to device 10, causing movement of head 12 between the insertion state and shape and the deployment state and shape.

As mentioned above, in some aspects, activator mechanism 36 and base 14 may further comprise cooperating locking mechanisms 28 that removably fix activator mechanism 36 to base 14. For example, in some aspects, cooperating locking mechanisms 28 may comprise a protruding structure opposing a key and groove structure, such that insertion of the protruding structure within the key, and movement into the groove, limits movement of activator mechanism 36 relative to base 14 in one or both of a direction parallel to and a direction rotationally about the extent of the body of activator mechanism 36, i.e. parallel to and/or rotationally about longitudinal axis 16. It should be noted that other locking mechanisms 28 may be utilized that fix activator mechanism 36 relative to base 14, such as through holes and pins, a corresponding groove and ridge which may be forced between locked and unlocked states, separate locking elements such as locking washers, friction fit elements, stepped members, etc.

Additionally, referring to FIGS. 9, 10 and 14-19, in some aspects, device 10 may further comprise a permeable section 74 operable, in some aspects, to allow for the passage of gases, but not liquids or solids, through head 12. For example, permeable section 74 may comprise a permeable material portion 76 on distal side 62 of head 12, where the permeable material portion 76 is connected to the material forming the remainder of device 10. In another example, permeable section 74 may comprise a pattern of micropores 78 formed on distal side 62 of head 12. For example, micropores 78 may be holes through permeable section 74 having a sufficiently small size such that liquid fluid resists passing through the hole, and in some aspects the holes may be sized to allow flatus gases may be allowed to pass. It should be noted that aspects of permeable section 74 may comprise either one of, or a combination of, permeable material portion 76 and a section of micropores 78. Additionally, permeable section 74 may comprise one or any number of layers of material, where in some aspects each layer may provide different performance characteristics. Further, for example, permeable section 74 may be formed from one or any combination of GORE-TEX® material, HyVent® material, H2No® material, Conduit™ laminate material, or other waterproof breathable material and/or any material having sufficiently small-sized openings to function as described herein. Permeable section 74 thereby allows gases that would normally build up within bodily cavity 24, due to seal 34 formed between device 10 and bodily cavity 24 and/or opening 22, to be expelled outside of body 44 through internal cavity 58 of device 10.

Additionally, referring to FIGS. 10, 12-14 and 16-17, in some aspects, device 10 may further comprise a scaffolding structure 80 positioned at least within the portion of internal cavity 58 corresponding to head 12 of device 10, if not throughout the full extent of internal cavity 58. In some aspects, scaffolding structure 80 comprises a material that separates adjacent portions of inner surface 54 of wall 52 from contacting each other, thereby providing a pathway for gases received through permeable section 74 to travel through internal cavity 58 and out opening 60 in base 14. As such, scaffolding structure 80 may be gas permeable. In other aspects, scaffolding structure 80 comprises an elastically deformable material, for example, which may aid in biasing head 12 to move from the insertion state and shape to the deployment state and shape. For example, scaffolding structure 80 may comprise a semi-rigid and/or a compressible material including, but not limited to, one or any combination of open cell sponge, open cell foam, closed cell foam, cotton, natural fiber woven material, synthetic woven material, etc., or any combination of the like with similar material characteristics.

Figure 18:
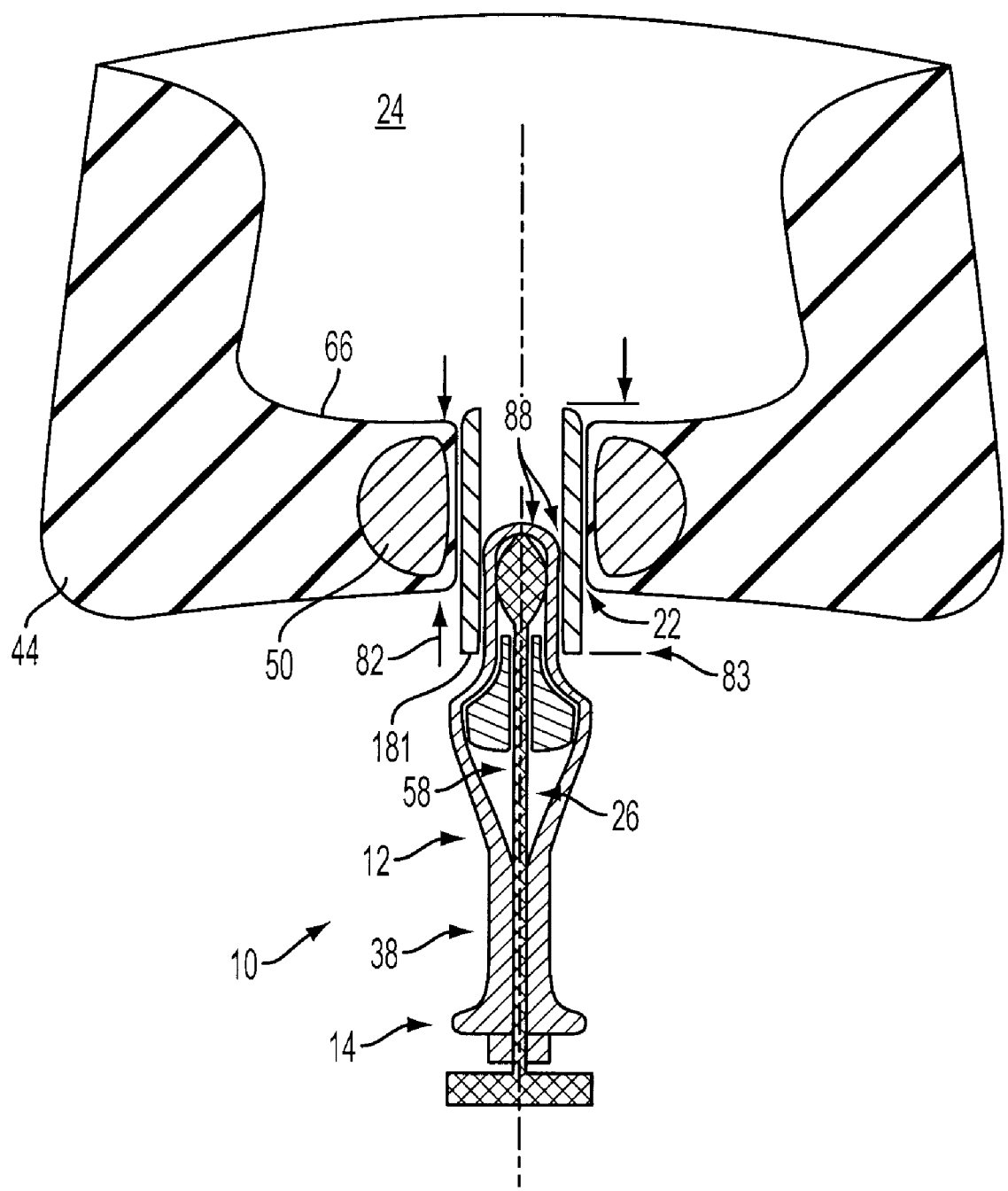
FIG. 18 is a partial cross-sectional view, similar to FIG. 13, and further including a deployment mechanism to assist with the insertion of the device through the bodily opening and into the bodily cavity.
Figure 22:
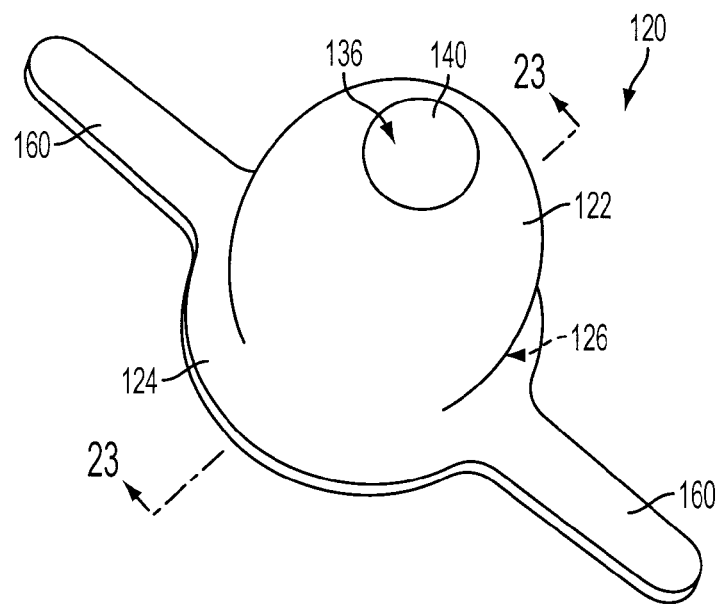
FIG. 22 is a perspective view of another aspect of an incontinence management device in an insertion state.

Further, referring to FIG. 18, a deployment mechanism 181 may be utilized to aid in the positioning, insertion and deployment of device 10. For example, deployment mechanism 181 may comprise a tubular body having a length 83 at least as long as the length 82 of opening 22, although in some aspects length 83 may be substantially greater than length 82 in order to improve the ease of inserting device 10. Further, in some aspects, deployment mechanism 181 may be comprise a relatively elastic material that allows for flexing and bending to further improve the ease and comfort associated with inserting device 10. In other aspects, however, deployment mechanism 181 may comprise a substantially rigid material that resists flexing and bending in order to provide a definitive insertion path. Additionally, it should be noted that in some aspects, the inner surface of deployment mechanism 181 may comprise at least a partial layer of a coating 84 of a low friction material in order to allow device 10 to slide through. In other aspects, outer surface 56 of device 10 may similarly comprise at least a partial coating of low resistance material in order to ease movement through deployment mechanism 181, and/or to ease movement through bodily opening 22. For example, coating 84 may comprise one or any combination of petroleum jelly, silicone, water-based lubricants (K-Y Brand Jelly, store brand equivalents, Astroglide® personal lubricant), wetable and/or hydrophobic materials and any other relatively lower friction (when compared to the friction existing without the coating), biocompatible material.

Referring to FIGS. 19-21, other aspects of an incontinence management device 90 may comprise a head 92 connected to a base 94, in some cases via a neck 96, wherein head 92, base 94 and neck 96 are substantially similar to previously discussed head 12, base 14 and neck 38, respectively. In these aspects, head 92 and neck 94 comprise a wall 98 having internal and external surfaces 100, 102, respectively. Internal surface 100 defines an internal cavity 104 substantially similar to internal cavity 58 discussed previously. Further, device 90 additionally includes an activator mechanism 106 movable between a first position (FIG. 20) corresponding to an insertion state of device 90, and a second position (FIG. 21) corresponding to a deployment state of device 90. In this case, the insertion state and deployment state of device 90 are substantially similar to the insertion state (FIG. 11) and the deployment state (FIG. 9) of device 10, discussed previously.

In this case, activator mechanism 106 may comprise a body 108 (FIG. 21) defined by an external surface 110 (FIG. 21). Body 108 may further comprise an internal wall 112 (FIG. 21) that defines a passageway 114 (FIG. 21) through body 108. For example, activator mechanism 106 may comprise one or any combination of a valve, filter, separator, etc. Activator mechanism 106 is movable relative to device 90, and base 94 in particular, between at least the first position (FIG. 20) wherein body 108 blocks and seals internal cavity 104 and the second position (FIG. 21) wherein passageway 114 is at least partially open to internal cavity 104. As such, in the first position, internal cavity 104 is sealed off from the exterior of device 90, whereas in the second position, internal cavity 104 is exposed to the exterior of device 90.

In some aspects, the apparatus described above may further comprise a drug delivery mechanism for delivering therapeutic agents/medications to local regions and/or generally to the body of the animal retaining the respective device. For example, the soft tissue in contact with and/or adjacent to the above devices generally are highly vascularized and loaded with nerve endings. As such, device 9, and/or 10 and/or 90 may include antithetic, hemorrhoidal medication or other therapy agents, for example, to reduce pain, repair tissue, and/or deliver gene therapy.

For example, in some aspects of device 9, and/or 10 and/or 90, the respective device may include an outer coating and/or layer along at least a portion of the exterior of the respective device, wherein the coating and/or layer comprises a drug and/or a carrier and the drug. In this aspect, the drug may include, but is not limited to, a therapeutically effective amount of one or any combination of an anesthetic such as lidocain, marcain, etc., an anti-hemorrhoidal and/or vasoconstricting medication, an itch-reducing medication such as hydrocortisone, a gene therapy medication, generic medicines, delivery of pharmaceutical devices and compounds or any other therapeutic material. The carrier may include, but is not limited to, one or any combination or any copolymer (where applicable) of a collagen, a silicone, a salve, a hydrogel, a bioabsorbable polymeric material, a biodegradable polymer, polylactic acid (PLA), polyglycolide or polyglycolic acid (PGA), copolymers of PLA and PGA, polylactic-co-glycolic acid (PLGLA), polyglycolic/poly(lactic acid) or PGLA, polycaprolactone (PCL), poly(acrylic acid)-g-PCL, poly-L-lactide acid (PLLA) poly-D-lactide acid (PDLA) or any other material capable of carrying a drug or therapeutic material, and/or any other material capable of being applied to, or capable of adhering to, the exterior surface of the respective device. Further, in some aspects, the carrier may comprise a semi-soluble or time-release characteristic or a controllable bioabsorption or biodegredation that allows for administering a controlled release of predetermined amounts of the drug/therapeutic agent over time.

In another example, in some aspects of device 9, and/or 10 and/or 90, the respective device may be formed, at least in part, by a material designed to release an impregnated drug and/or therapeutic agent. Such a material may include, but is not limited to, the elastically-deformable materials described above and/or the carrier materials described above. Further, for example, in some aspects, permeable section 74 (FIGS. 9, 10 and 14-19) may carry the above-described drug and/or therapeutic agent.

For example, in operation, internal cavity 104 may comprise a chamber having a lower environmental pressure, up to a vacuum environment, relative to the external environmental pressure outside of device 90. For instance, normal atmospheric pressure may exist external to device 90, while internal cavity 104 is evacuated, and the vacuum is maintained by moving activator mechanism 106 to the second position, as described above, or alternatively by removing the activator mechanism. Device 90 may be formed into the above-described insertion shape during the evacuation of internal chamber 104, either manually or through the use of a form. In any case, wall 98 of device 90 may be sized such that the insertion shape may be maintained while internal cavity 104 is at the relatively low pressure than the external environment. Optionally, as described above, scaffolding structure (76, FIG. 10) may be utilized to help device 90 maintain the insertion shape. Further, upon moving activator mechanism 106 into the first or open position (FIG. 21), where passageway 114 fluidly connects with internal cavity 104, the pressure within the cavity will equalize with the external pressure, thereby causing device 90 to move into deployment position and deployment shape, substantially sealing bodily cavity 24 (such as in FIG. 14). As such, device 90 may comprise an elastic material, where the insertion shape comprises a temporarily deformed shape of the device and where the deployment shape is the natural shape to which the device is biased to return. Further, activator mechanism 106 is movable between the first position and the second position relative to device 90, causing movement between the insertion state and shape and the deployment state and shape.

Referring to FIGS. 22-25, other aspects of an incontinence management device 120 may comprise a head 122 connected to a base 124, in some cases via a neck 126, wherein head 122, base 124 and neck 126 are substantially similar to previously discussed head 12, base 14 and neck 38, respectively. In these aspects, head 122 and neck 124 comprise a wall 128 (FIGS. 23 and 25) having internal and external surfaces 130, 132, respectively. Internal surface 130 defines an internal cavity 134 substantially similar to internal cavity 58 discussed previously. Further, device 120 additionally includes an activator mechanism 136 movable between a first position (FIG. 23) corresponding to an insertion state of device 120, and a second position (FIG. 25) corresponding to a deployment state of device 120. In this case, the insertion state and deployment state of device 120 are substantially similar to the insertion state (FIG. 11) and the deployment state (FIG. 9) of device 10, and of the similar states of device 9, discussed previously.

Figure 23:
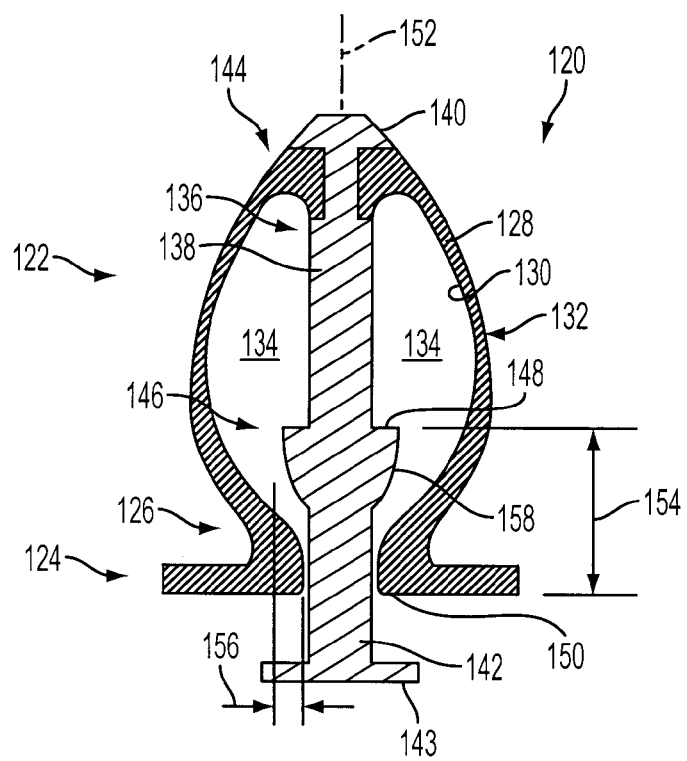
FIG. 23 is a cross-sectional view of the device of FIG. 22 along line 23-23.
Figure 24:
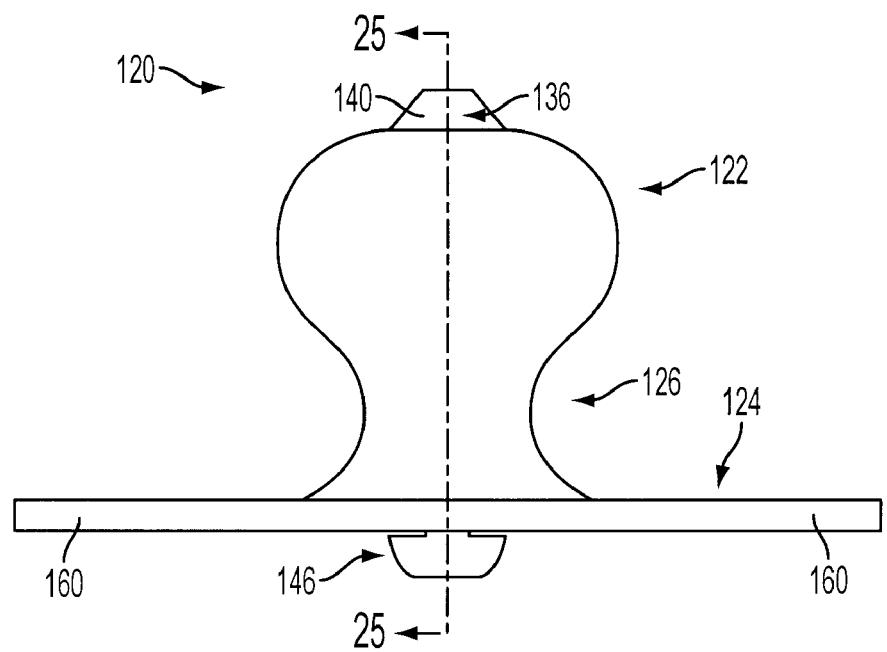
FIG. 24 is a side view of the device of FIG. 22 in a deployed state.

In this case, activator mechanism 136 may comprise a stem-like body 138 extending between an anchor end 140 (FIGS. 23 and 25) and a gripping end 142 (FIG. 23). Activator mechanism 136 may be separately or integrally formed with head 122 and/or base 124. In some aspects, body 138 may be a structure having sufficient rigidity to avoid substantial bending during the insertion and/or deployment processes, while in other aspects body 138 may comprise a flexible structure, such as a string, cord, strand, etc. Anchor end 140 is connected to a distal side 144 of head 122, while gripping end 142 extends away from device 120 adjacent to base 124. In some aspects, gripping end 142 may include gripping structure 143 extending away from body 138 to provide additional structure to grasp during operation of activator mechanism 136. For example, gripping end 142 may include one or more flanges, a ring, an enlarged spherical structure, etc. Activator mechanism 136 is movable between a first position (FIG. 23) corresponding to the insertion state and shape of device 120, and a second position (FIG. 25) corresponding to the deployment state and shape of device 120. In some aspects, activator mechanism 136 actuates the insertion state and the deployment state.

Further, device 120 comprises a locking mechanism 146 (FIGS. 23-25) operable to removably secure activator mechanism 136 relative to device 120, thereby removably fixing device 120 in at least one state, such as the deployment state. For example, in some aspects, locking mechanism 146 cooperates with activator mechanism 136 to fix device 120 in one or both states. As such, locking mechanism 146 may be movable in conjunction with, or movable independent of, activator mechanism 136.

Figure 25:
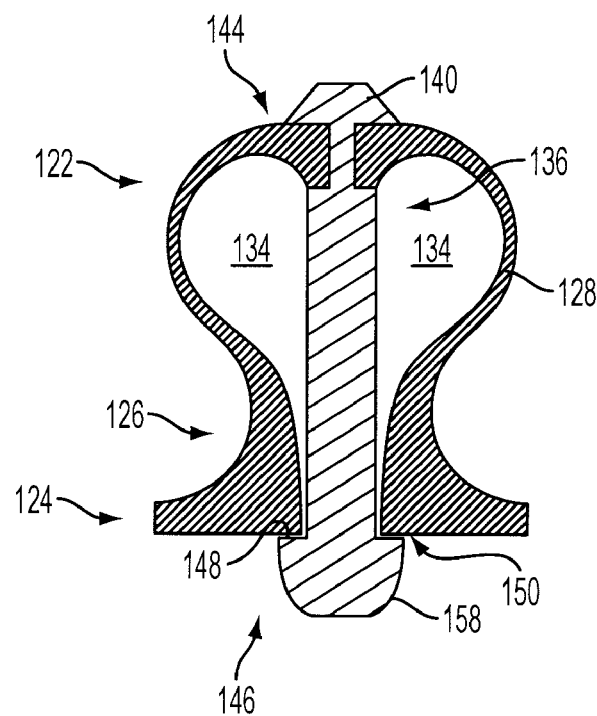
FIG. 25 is a cross-sectional view of the device of FIG. 24 along line 25-25.
Figure 26:
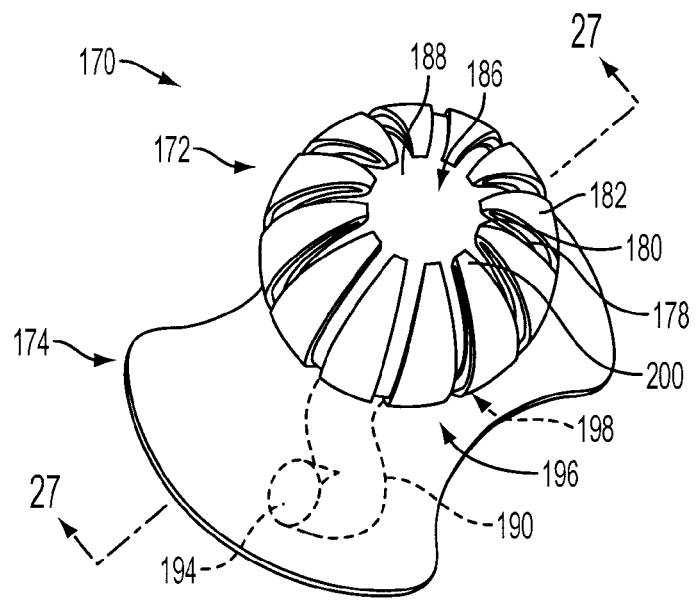
FIG. 26 is a perspective view of another aspect of an incontinence management device in an insertion state.

For example, in some aspects, locking mechanism 146 may comprise a first engagement portion 148, such as a projection extending from body 138 of activator mechanism 136, and a second engagement portion 150, such as a wall or flange associated with base 124, which are relatively movable relative to an axis 152 between a disconnected state (see FIG. 23) and a connected state (see FIG. 25). In the disconnected state, activator mechanism 136 and base 124 may not be secured together, while in the connected state they are removably fixed together. For example, in some aspects, activator mechanism 136 is moved a predetermined distance 154 along axis 152 in order to fix device 120 in the deployment state. Also, during movement from the disconnected state to the connected the state, one or both of first engagement portion 148 and second engagement portion 150 may be elastically deformable by an amount equal to a predetermined engagement distance 156. Predetermined engagement distance 156 corresponds to an amount of interference or overlap between opposing surfaces of first and second engagement portions 148, 150 that cause activator mechanism 136 and base 124 to be securely connected together. Additionally, locking mechanism 146 may further comprise a ramp structure 158, having a surface extends obliquely relative to the direction of movement such that its cross section increases during movement from the disconnected state to the connected state. Generally, ramp structure 158 provides a smooth transition from the disconnected state up to initiation of the connected state, as the thickest portion of ramp structure 158 is located adjacent to the corresponding engagement portion 148, 150.

It should be noted that locking mechanism 146 may comprise many other structures for fixing device 120 in one or both of the insertion state and the deployment state. For example, locking mechanism 146 may comprise a key and keyhole structure, wherein a protruding portion of activator mechanism 136 may fit through a keyhole and then be rotated and held away from the keyhole to fix the state of device 120. Further, locking mechanism 146 may comprise a thread and screw structure, such as activator mechanism 136 being rotatable and having a screw structure, and base 124 threadingly receiving the screw structure to fix the state of the device. Additionally, locking mechanism 146 may comprise a separate device, such as a lock pin positioned in a hole through activator mechanism 136 or a lock washer engaging a channel in activator mechanism 136.

Further, it should be noted that in aspects including locking mechanism 146 at least partially formed on body 138 of activator mechanism 136, the portion of body 138 between the locking mechanism 146 and gripping end 142 may be removable from device 120 (compare FIGS. 23 and 25). For example, removing this section of body 138 reduces the protrusion of the end of body 138 from the device 120, thereby enhancing the operational comfort of device 120.

Additionally, in some aspects, base 124 may further include one or more flanges 160 (FIGS. 22 and 24) extending away from axis 152. The one or more flanges 160 may aid in placement of device 120 during insertion, and may further aid in securing the device in place after deployment by engaging corresponding features in the body, or by providing a contact surface for external fixation mechanisms, such as tape. Further, for example, flange 160 may also be used as a secondary sealing mechanism or a handle/removal device.

Figure 14:
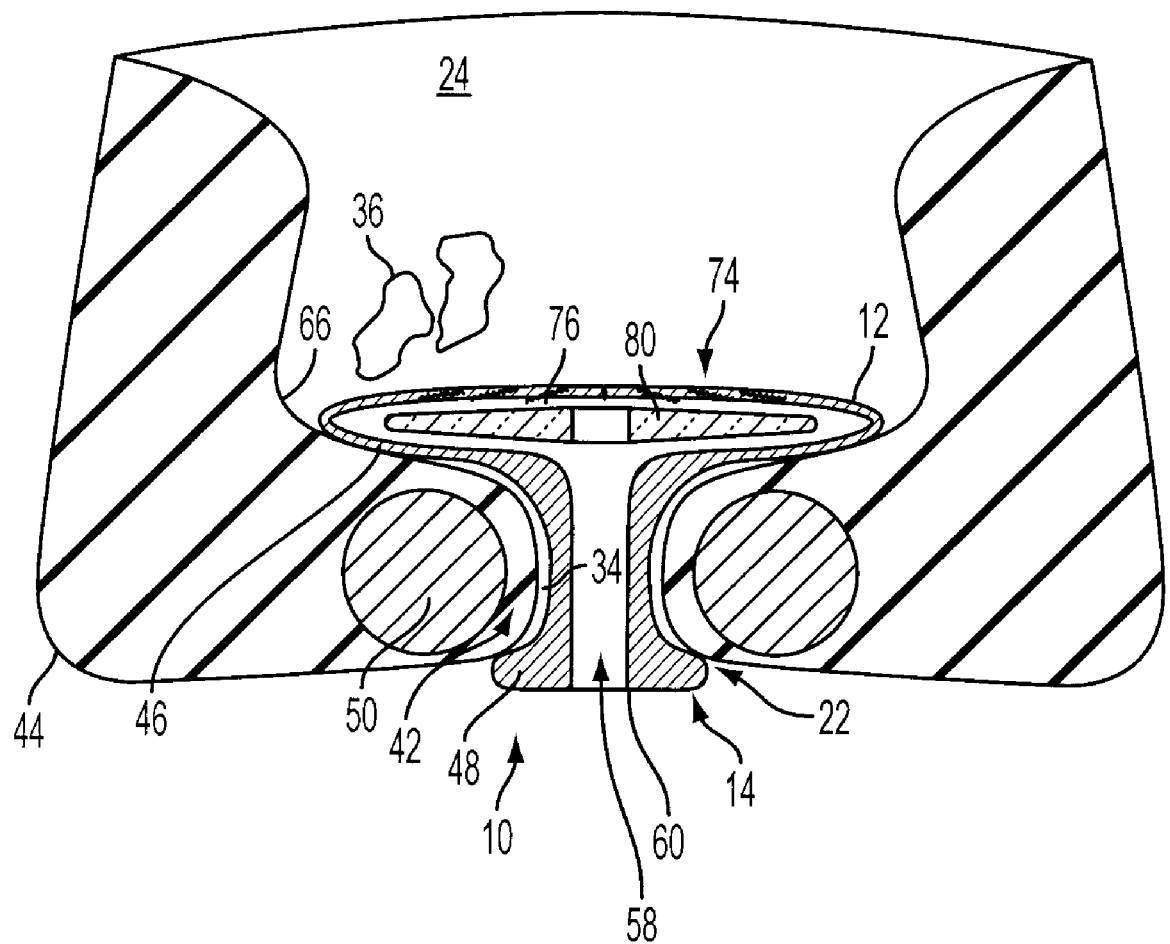
FIG. 14 is a partial cross-sectional view similar to FIG. 13, but with the device in the deployed state within the opening and the bodily cavity.
Figure 15:
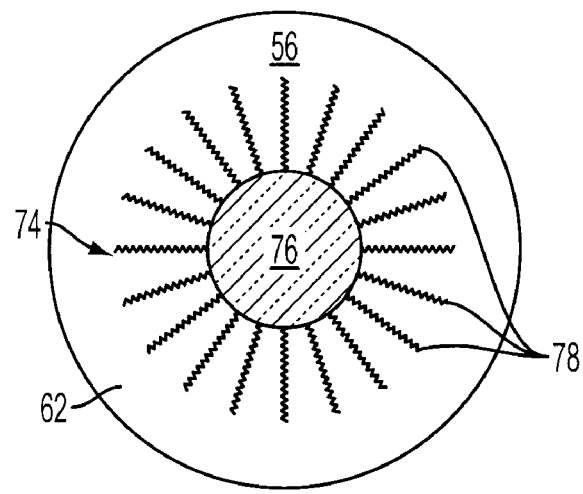
FIG. 15 is a top view of the device of FIG. 9, including one aspect of a permeable section.
Figure 16:
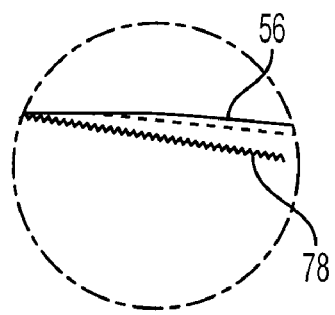
FIG. 16 is a close-up side view of the noted section of FIG. 9, including one aspect of permeable micropores.
Figure 17:
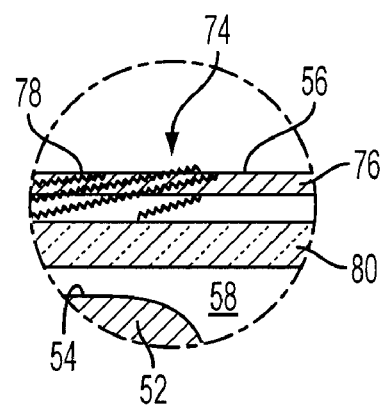
FIG. 17 is a close-up cross-sectional view of the noted section of FIG. 10, including one aspect of a scaffolding structure within an internal cavity of a head of the device, and further including a permeable section.

Referring to FIGS. 26-29, other aspects of an incontinence management device 170 may comprise a head 172 connected to a base 174, in some cases via a neck 176, wherein head 172, base 174 and neck 176 are substantially similar to previously discussed head 11 (FIGS. 1-7) and head 12 (FIGS. 9-18), base 15 (FIGS. 1-7) and base 14 (FIGS. 9-18), and neck 13 (FIGS. 1-7) and neck 38 (FIGS. 9-18), respectively. In these aspects, head 172 and neck 174 comprise a wall 178 (FIGS. 23 and 25) having internal and external surfaces 180, 182, respectively. Internal surface 180 defines an internal cavity 184 similar to internal cavity 58 (FIG. 10) discussed previously. Further, device 170 additionally includes an activator mechanism 186 having a body 188 movable between a first position (FIGS. 26-27) corresponding to an insertion state of device 170, and a second position (FIGS. 28-29) corresponding to a deployment state of device 170. In this case, the insertion state and deployment state of device 170 are substantially similar to the insertion state (FIG. 11) and the deployment state (FIG. 9) of device 10, and the similar states of device 9, discussed previously. For example, in some aspects, activator mechanism 86 may comprise a material conformable to fit within internal cavity 184 in the first position, and which expands and moves into the second position upon absorbing bodily liquid fluids from within a bodily cavity, such as fluid/waste/excrement 36 (FIG. 14) of bodily cavity 24 (FIG. 14). For instance, such a material may be a hydrophilic material, such as hydrogel, biogel, etc. Additionally, device 170 may include a retrieval mechanism 190 having an anchor end 192 connected to the device 170 and a gripping end 194 extending from the device 170. For example, retrieval mechanism 190 may comprise a flexible, elongated member, such as a fiber or a string, etc., that a user may grab and pull on to remove the device 170 from the bodily cavity 24 (FIG. 146).

Thus, in these aspects, head 172 and activator mechanism 186 are both movable between an insertion shape (FIGS. 26-27), where head 172 and activator mechanism 186 are sized for insertion within a bodily opening 22 (FIGS. 13-14), and a deployment shape (FIGS. 28-29), where head 172 and activator mechanism 186 are sized to form a seal 34 (FIG. 14) that prevents fluid/waste/excrement 36 (FIG. 14) from exiting bodily cavity 24 (FIG. 14) through opening 22 (FIG. 14).

In some aspects, head 172 comprise a plurality of elongated members 196 connected at a base end 198 adjacent to base 174 and/or neck 176, and relatively movable along their lengths up to an opposing free end 200. As such, each of the plurality of elongated members 196 may be separately movable, thereby allowing each respective member to individually conform to the internal anatomy of the respective bodily cavity 24 (FIG. 14) to provide effective sealing. It should be noted, however, that head 172 may be formed from a unitary material having comparable expansion capabilities.

In some aspects, base 174 comprises one or more flanges 202 extending away from the device 170. Base 174 and/or flanges 202 may limit the amount of insertion of device 170 into a bodily cavity, and flanges 202 may further aid in securing device 170 in position.

In some aspects, retrieval mechanism 190 extends through a portion of internal cavity 184 that extends through neck 176 and/or base 174. Anchor end 192 may comprise a body that extends away from retrieval mechanism 190 and contacts or is fixed to portions of internal cavity 184 within head 172.

In other aspects, an incontinence control device may comprise a solid structure having a head movable between a first and second state, as described. For example, head may be formed from a hydrophilic material. The first state may comprise the deployed shape, which may be the natural shape of the device when hydrated. The device may be formed by hydrating the head, then stretching the head into the deployment shape, i.e. the second state, and holding the head in this shape while dehydrating the material. As such, the device can be maintained in the insertion state. When ready for deployment, the device can then be inserted into a bodily cavity. After insertion, the device will hydrate upon absorbing bodily liquid fluid, thereby causing the device to change into the deployment shape and sealing the bodily cavity.

Thus, the described aspects include incontinence management devices having a head that changes from a first shape, sized for insertion within an opening to a bodily cavity, to a second shape, sized for sealing the opening. In some aspects, the head may include a hollow interior chamber, while in other aspects the head may comprise a solid structure. Further, these devices may include a base that limits the amount of insertion of the head within the opening and/or within the bodily cavity. In some aspects, the head and base may be connected by a neck, which also may be sized to seal the opening to the bodily cavity. Additionally, the incontinence management devices include an activator mechanism movable from a first position to a second position, relative to the device. The first position of the activator mechanism corresponds with an insertion state of the device, while the second position corresponds to a deployment state. In some aspects, movement of the activator mechanism may actuate one and/or both states of the respective incontinence management device. Further, in some aspects, deployment mechanisms may be utilized to position and insert the respective incontinence management device. Additionally, in some aspects, the activator mechanism may also be utilized to control the position of the device, while in other aspects a retrieval mechanism may be utilized to remove the device.

In some aspects, the incontinence management device may substantially comprise a resorbable material, compatible with the body into which it is inserted, and which dissolves and/or degrades in a non-harmful manner after a predetermined time in contact with bodily liquid fluids. Such incontinence management devices advantageously provide an incontinence management mechanism that automatically removes itself from blocking/sealing the opening, and thereby automatically allows for the natural bodily function. In other aspects, non-resorbable materials may be utilized. In any case, the present aspects provide simple, efficient and easily manipulated devices for use in managing incontinence and/or in sealing the outflow of bodily liquid, and in some aspects gaseous, fluids from a bodily cavity.

Further, in some aspects, the incontinence management device may include a gas-permeable portion, such as a permeable membrane and/or a section having micropores. The gas-permeable portion allows internal gas pressure from within the bodily cavity to be relieved by allowing passage of gas through the device while restricting the flow of liquid fluid.

Additionally, in some aspects, any of devices 9, 10, 90, 120, and 170 may be packaged in a kit with one or more of a lubricant, a therapeutic agent, a carrier or carrier layer for the therapeutic agent, a retrieval mechanism, and a deployment mechanism.

While the foregoing disclosure includes illustrative aspects, it should be noted that various changes and modifications could be made herein without departing from the scope of these described aspects as defined by the appended claims. Furthermore, although elements of the described aspects may be described or claimed in the singular, the plural is contemplated unless limitation to the singular is explicitly stated. Additionally, all or a portion of any aspect of the invention may be utilized with all or a portion of any other aspect. Further, although specific terms are employed herein, they are used in a generic and descriptive sense only and not for purposes of strict limitation unless otherwise specified. Therefore, it is to be understood that the invention is not to be limited to the specific aspects disclosed and that modifications and other aspects are intended to be included within the scope of the appended claims.

What is claimed is:

1. An incontinence management device, comprising:
   a base sized to limit insertion of the incontinence management device into an anal cavity having a dentate line;
   a head having a first state and a second state, wherein in the first state the head is sized for insertion within the anal cavity, and wherein in the second state the head is sized to substantially seal the anal cavity above the dentate line;

a neck connected to and extending between the base and the head, wherein the neck comprises a predetermined length to position the head beyond the dentate line when the incontinence management device is located at a deployed position within the anal cavity;

an external surface defining the head, the neck and the base;

an internal wall defining an internal cavity extending through the head the neck and the base to an opening in the base, wherein the internal cavity separates a distal side and a proximal side of the head relative to the opening wherein the head further comprises a permeable section on the distal side wherein the permeable section allows passage of gases and resists passage of liquids and solids;

a scaffolding structure positioned in the internal cavity within at least the head, wherein the scaffolding structure is positioned to separate adjacent portions of the internal wall within the head in the second state, wherein the scaffolding structure is gas permeable, wherein the scaffolding structure comprises a pathway through the head to the internal cavity in the neck and the opening in the base for the gases received through the permeable section of the head; and a deployment device having an internal deployment cavity extending between an insertion end and an open end, wherein the head, the neck and the base are positionable within the deployment device when the head is in the first state.

2. The device of claim 1, wherein the predetermined length is sized to position the head beyond the dentate line when the base contacts an opening to the anal cavity.

3. The device of claim 1, wherein the predetermined length ranges from about 2 centimeters (cm) to about 5 cm.

4. The device of claim 1, wherein the predetermined length ranges from about 2.5 centimeters (cm) to about 3 cm.

5. The device of claim 1, wherein the head has a diameter ranging from about 1.5 cm to about 5 cm.

6. The device of claim 1, wherein the head has a diameter ranging from about 2.5 cm to about 4.5 cm.

7. The device of claim 1, further comprising a therapeutic agent carried by at least one of the head, the neck and the base.

8. The device of claim 7, further comprising a carrier attached to at least one of the head, the neck and the base, wherein the therapeutic agent is contained within the carrier.

9. The device of claim 1, further comprising:

an activator movably connected to the internal cavity and, wherein the activator is movable between a first position and a second position, wherein the first position maintains the head in the first state, and wherein the second position allows the head to change to the second state.

10. The device of claim 9, wherein the activator comprises a valve.

11. The device of claim 9, wherein the activator comprises a predetermined activator length such that the activator extends from the head to outside of the base when the head is in the first state.

12. The device of claim 1, wherein the head comprises an external surface opposite the neck, wherein the external surface comprises a convex shape.

13. The device of claim 12, wherein the head comprises an internal surface connected to the neck, wherein the internal surface comprises a concave shape.

14. The device of claim 1, wherein the head further comprises a length parallel to a first axis and a width parallel to a second axis different from the first axis, wherein the head is movable between a first shape having a first width operable to permit insertion into the anal cavity and a second shape having a second width operable to seal the anal cavity.

15. The device of claim 1, wherein the deployment device further comprises an activator movable between a pre-deployment position and a deployed position within the internal deployment cavity, wherein the activator comprises an activator length extending between a first end and a second end, wherein the first end is operable to contact the base to urge incontinence management device out of the deployment device through the insertion end during movement of the activator from the pre-deployment position to the deployed position.

16. The device of claim 1, further comprising a therapeutic material.

17. The device of claim 1, wherein the scaffolding structure comprises an elastically deformable material operable to bias the head into the second state.

18. The device of claim 1, wherein the permeable section comprises micropores having a sufficiently small size to resist flowing through of a liquid fluid.

19. The device of claim 1, wherein the head substantially comprises a resorbable material.

20. A method of managing incontinence, comprising:
obtaining a device comprising:
a base sized to limit insertion of the incontinence management device into the anal cavity;
a head having a first state and a second state, wherein in the first state the head is sized for insertion within the anal cavity, and wherein in the second state the head is sized to substantially seal the anal cavity; and
a neck connected to and extending between the base and the head, wherein the neck comprises a predetermined length to position the head beyond the dentate line when the incontinence management device is located at an operating position within the anal cavity;
inserting the device, with the head in the first state, through an anal canal and into an anal cavity such that the head precedes the neck and the base;
positioning the device within the anal cavity so that the head is inserted beyond the dentate line within the anal cavity, and so that the head is operable to change to the second state and form a seal with the anal cavity at a location within the anal cavity beyond the dentate line; and
removing the device from the anal cavity using a retrieval mechanism having an anchor end connected to the device and a gripping end extending from the device and extending outside of the anal cavity.

21. The method of claim 20, wherein inserting further comprises containing the device within a deployment mechanism having an activator mechanism, inserting the deployment mechanism within the anal cavity, and wherein positioning the device further comprises moving the activator mechanism to deploy the device.

22. The method of claim 20, further comprising allowing the device to degrade within the anal cavity according to a predetermined biodegradation characteristic.

23. The method of claim 20, further comprising releasing a therapeutic agent from the device.

24. The method of claim 20, further comprising allowing gas to pass through the device.

25. The method of claim 20, wherein obtaining further comprises obtaining a device comprising:
an external surface defining the head, the neck and the base;

an internal wall defining an internal cavity extending through the head, the neck and the base to an opening in the base, wherein the internal cavity separates a distal side and a proximal side of the head relative to the opening;

wherein the head further comprises a permeable section on the distal side, wherein the permeable section allows passage of gases and resists passage of liquids and solids; and a scaffolding structure positioned in the internal cavity within at least the head, wherein the scaffolding structure is positioned to separate adjacent portions of the internal wall within the head in the second state, wherein the scaffolding structure is gas permeable, wherein the scaffolding structure comprises a pathway through the head to the internal cavity in the neck and the opening in the base for the gases received through the permeable section of the head.

26. The method of claim 25, wherein obtaining further comprises obtaining a device wherein the scaffolding structure comprises an elastically deformable material operable to bias the head into the second state.

27. An incontinence management device, comprising:

a head having a first state and a second state, wherein in the first state the head is sized for insertion within a predetermined body orifice operable to eject digestive by-products, and wherein in the second state the head is sized to substantially seal the predetermined body orifice;

a layer on the head, the layer comprising a therapeutic material;

a base operable to limit insertion of the device into the predetermined body orifice;

a neck connected to and extending between the head and the base;

an external surface defining the head, the neck and the base;

an internal wall defining an internal cavity extending through the head, the neck and the base to an opening in the base, wherein the internal cavity separates a distal side and a proximal side of the head relative to the opening;

wherein the head further comprises a permeable section on the distal side, wherein the permeable section allows passage of gases and resists passage of liquids and solids; and a scaffolding structure positioned in the internal cavity within at least the head, wherein the scaffolding structure is positioned to separate adjacent portions of the internal wall within the head in the second state, wherein the scaffolding structure is gas permeable, wherein the scaffolding structure comprises a pathway through the head to the internal cavity in the neck and the opening in the base for the gases received through the permeable section of the head.

28. The device of claim 27, wherein the head substantially comprises a resorbable material.

29. An incontinence management device, comprising:

a base sized to limit insertion of the incontinence management device into an anal cavity having a dentate line;

a head having a first state and a second state, wherein in the first state the head is sized for insertion within the anal cavity, and wherein in the second state the head is sized to substantially seal the anal cavity above the dentate line;

a neck connected to and extending between the base and the head, wherein the neck comprises a predetermined length to position the head beyond the dentate line when the incontinence management device is located at a deployed position within the anal cavity;

an external surface defining the head, the neck and the base;

an internal wall defining an internal cavity extending through the head the neck and the base to an opening in the base, wherein the internal cavity separates a distal side and a proximal side of the head relative to the opening wherein the head further comprises a permeable section on the distal side wherein the permeable section allows passage of gases and resists passage of liquids and solids;

a scaffolding structure positioned in the internal cavity within at least the head, wherein the scaffolding structure is positioned to separate adjacent portions of the internal wall within the head in the second state, wherein the scaffolding structure is gas permeable, wherein the scaffolding structure comprises a pathway through the head to the internal cavity in the neck and the opening in the base for the gases received through the permeable section of the head; and an activator movably connected to the internal cavity and, wherein the activator is movable between a first position and a second position, wherein the first position maintains the head in the first state, and wherein the second position allows the head to change to the second state, wherein the activator comprises a valve.

30. The device of claim 29, further comprising a therapeutic material.

* * * * *